United States Patent [19]

Shimizu et al.

[11] Patent Number: 4,956,462
[45] Date of Patent: Sep. 11, 1990

[54] "TRIAZOLO-PYRIMIDINE INTERMEDIATES"

[75] Inventors: Shigeo Shimizu; Hiroyuki Takano, both of Mukawa, Japan

[73] Assignees: Sankei Pharmaceutical Co., Ltd., Tokyo; Nippon Pharmaceutical Development Institute Co., Ltd., Hokkaido, both of Japan

[21] Appl. No.: 357,124

[22] Filed: May 26, 1989

Related U.S. Application Data

[62] Division of Ser. No. 222,404, Jul. 21, 1988.

[30] Foreign Application Priority Data

Aug. 7, 1987 [JP] Japan ................. 62-196178

[51] Int. Cl.$^5$ ................. C07D 487/04; A61K 31/505
[52] U.S. Cl. ....................... 544/263; 544/262; 544/280; 544/281; 540/227
[58] Field of Search ............... 544/262, 263, 281, 280

[56] References Cited

U.S. PATENT DOCUMENTS

| | | | |
|---|---|---|---|
| 3,799,926 | 3/1974 | Duffin et al. | 544/263 |
| 4,528,288 | 7/1985 | Wade | 544/363 |
| 4,657,172 | 6/1987 | Quan et al. | 544/263 |

FOREIGN PATENT DOCUMENTS 0150507 8/1985 European Pat. Off. .

*Primary Examiner*—Nicholas S. Rizzo
*Attorney, Agent, or Firm*—Antonelli, Terry, Stout & Kraus

[57] ABSTRACT

There are disclosed a β-lactam compound represented by the formula (I):

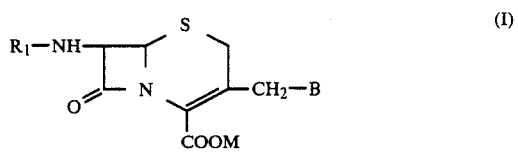

wherein $R_1$ represents an acyl group; M represents a hydrogen atom, a protective group of an eliminatable group which is easily hydrolyzable in a human body; B represents a group represented by the formula (b):

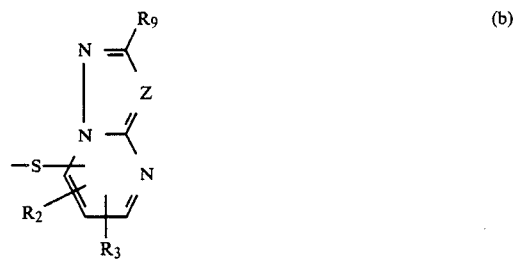

where at least one of $R_2$, $R_3$ and $R_9$ represent a group represented by the formula: $-A-OR_4$ where $R_4$ represents a hydrogen or a lower alkyl group; and A represents a straight or branched alkylene group having 1 to 6 carbon atoms; and a remaining group or groups are each independently a hydrogen atom; a cyano group; a lower alkyl group which may be substituted by a halogen atom; a carbamoyl group which may be substituted by a lower alkyl group; a cycloalkyl group; or a carboxyl group which may be substituted by a protective group of an eliminatable group which is easily hydrolyzable in a human body, and also when $R_9$ is $-A-OR_4$, $R_2$ and $R_3$ may be combined with each other to form an alkylene group having 3 to 4 carbon atoms; and Z represents a nitrogen atom or a group represented by the formula: $C-R_{10}$ where $R_{10}$ represents a hydrogen atom, a carboxyl group or a lower alkyl group which may be substituted by a hydroxy group or a lower alkoxy group, or its pharmaceutically acceptable salt, and a process for preparing the same, an intermediate for synthesis of the same and a medicinal composition for bacterially infectious disease therapy containing the same.

3 Claims, No Drawings

"TRIAZOLO-PYRIMIDINE INTERMEDIATES"

This is a division of application Ser. No. 222,404, filed July 21, 1988.

BACKGROUND OF THE INVENTION

This invention relates to novel β-lactam compounds, more particularly to a novel cephalosporin series compound useful for antibiotics, a method for preparing the same, a synthetic intermediate and use thereof.

Heretofore, it has been known that β-lactam series antibiotics have antibacterial activities to gram positive bacteria and gram negative bacteria and many of these compounds have actually been applied therefor. Among them, compounds which are called to as the third generation cephalosporin series antibiotics have wide range of antibacterial spectrum and particularly are evaluated in the clinical field.

However, while the several kinds of the above compounds have been used in practical use, all of them are inferior in their antibacterial activities to *Pseudomonos aeruginosa*. Further, some kinds of them are finely effective to gram negative bacteria other than *Pseudomonos aeruginosa* but there are disadvantages that they have lower activities to gram positive bacteria and also, accompanied with the increased frequency in use of cephalosporins, strains which aquired cross resistance to β-lactams are gradually increasing.

SUMMARY OF THE INVENTION

The present inventors have intensively studied, by referring to the above situation, concerning a compound which has potent antibacterial activities in extremely wide ranges, and as a result, have found that the compound represented by the formula (I) has excellent characteristics as a medicinal composition for bacterially infectious disease (microbism) therapy and accomplished the present invention.

That is, the present invention relates to a β-lactam compound represented by the formula (I):

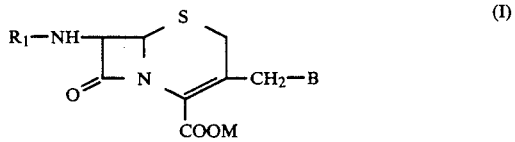

wherein $R_1$ represents an acyl group; M represents a hydrogen atom, a protective group or an eliminatable group which is easily hydrolyzable in a human body; B represents a group represented by the formula (b):

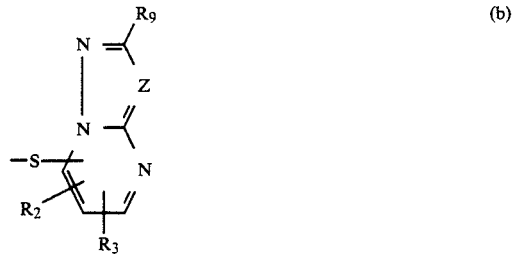

where at least one of $R_2$, $R_3$ and $R_9$ represent a group represented by the formula: $-A-OR_4$ where $R_4$ represents a hydrogen or a lower alkyl group; and A represents a straight or branched alkylene group having 1 to 6 carbon atoms; and a remaining group or groups are each independently a hydrogen atom; a cyano group; a lower alkyl group which may be substituted by a halogen atom; a carbamoyl group which may be substituted by a lower alkyl group; a cycloalkyl group; or a carboxyl group which may be substituted by a protective group or an eliminatable group which is easily hydrolyzable in a human body, and also when $R_9$ is $-A-OR_4$, $R_2$ and $R_3$ may be combined with each other to form an alkylene group having 3 to 4 carbon atoms; and Z represents a nitrogen atom or a group represented by the formula: $C-R_{10}$ where $R_{10}$ represents a hydrogen atom, a carboxyl group or a lower alkyl group which may be substituted by a hydroxy group or a lower alkoxy group, or its pharmaceutically acceptable salt, a method for preparing the same, an intermediate for synthesis thereof and a medicinal composition for bacterially infectious disease therapy containing said compound as the active ingredient.

Further, hydrates or organic solvates of the compound represented by the above formula (I) are included in the scope of the present invention as a matter of course.

DESCRIPTION OF THE PREFERRED EMBODIMENTS

Next, each groups which are summarily shown in the above formula (I) are explained in more detail.

Explanation of $R_1$

An acyl group represented by $R_1$ can be derived from a carboxylic acid, and includes all organic groups used in cephalosporanic chemistry.

Particularly preferred acyl group may include a 2-(2-thienyl)acetyl group and a group represented by the formula (C):

wherein $R_7$ represents a heterocyclyl group; and $R_8$ represents a hydrogen atom, a lower alkyl group or a group represented by the formula (d), (e) or (f):

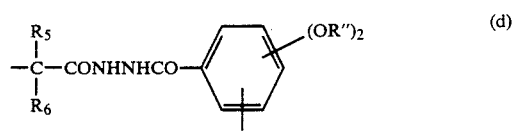

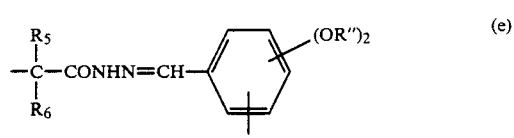

where $R_5$ and $R_6$ each independently represent a hydrogen atom or a lower alkyl group; R″ represents a hydrogen atom or a protective group; and X represents a hydrogen atom, a lower alkyl group, a lower alkoxy group or a halogen atom, or a group represented by the formula (g):

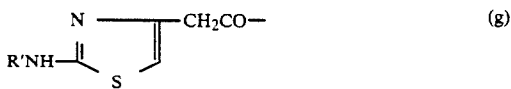 (g)

wherein R' represents a hydrogen atom or a protective group,
and an acyl group as disclosed in Japanese Provisional Patent Publications Nos. 16487/1987, 33185/1987, 108997/1977, 49382/1983, 74680/1983, 139381/1984, 167576/1984, 163884/1985 267583/1986.

In the above, an acyl group represented by the formula (a) is preferred for injection.

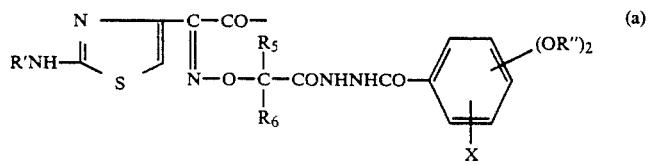 (a)

wherein $R_5$, $R_6$, R', R'' and X have the same meanings as defined above.

In the above, as a lower alkyl group represented by $R_5$, $R_6$ and $R_8$, there may be mentioned a straight or branched alkyl group having 1 to 3 carbon atoms. For example, there may be mentioned a methyl group, an ethyl group, an n- or iso-propyl group, etc. As the protective group represented by the R', there may be mentioned a diphenylmethyl group, a t-butyl group, a p-nitrobenzyl group, a trimethylsilyl group, etc. As the protective group represented by the R'', there may be mentioned a lower acyl group such as an acetyl group, a propionyl group, etc. and a lower alkoxycarbonyl group such as a methoxycarbonyl group, an ethoxycarbonyl group, etc. As the halogen atom represented by X, there may be mentioned a chlorine atom, a bromine atom, a fluorine atom, etc., and as the lower alkyl group, there may be mentioned a straight or branched alkyl group having 1 to 3 carbon atoms, for example, a methyl group, an ethyl group, an n- or iso-propyl group, etc., and as the lower alkoxy group, there may be mentioned an alkoxy group having 1 to 3 carbon atoms, for example, a methoxy group, an ethoxy group, an n- or isopropoxy group, etc.

Explanation of M

M is a hydrogen atom, a protective group or an eliminatable group which is easily hydrolyzable in a human body.

When the M is a protective group, there may be mentioned a diphenylmethyl group, a t-butyl group, a p-nitrobenzyl group, a trimethylsilyl group, etc.

Further, when the M is an eliminatable group which is easily hydrolyzable in a human body, there may be mentioned an acetoxymethyl group, an α-acetoxyethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group, a 5-methyl-2-oxo-1,3-dioxol-4-yl-methyl group and the like.

Explanation of $R_2$, $R_3$ and $R_9$

At least one of $R_2$, $R_3$ and $R_9$ is/are a group represented by the formula: $-A-OR_4$; and a remaining group or groups are each independently represent a hydrogen atom, a cyano group, a lower alkyl group which may be substituted by a halogen atom, a carbamoyl group which may be substituted by a lower alkyl group, a cycloalkyl group, or a carboxyl group which may be substituted by a protective group or an eliminatable group which is easily hydrolyzable in a human body, and also when $R_9$ is $-A-OR_4$, $R_2$ and $R_3$ may be combined with each other to form an alkylene group having 3 to 4 carbon atom.

In the above, as the lower alkyl group which may be substituted by a halogen atom, there may be mentioned, for example, a methyl group, an ethyl group, an n- or isopropyl group, a monofluoromethyl group, a di-fluoromethyl group, a trifluoromethyl group, a monofluoroethyl group, a difluoroethyl group, a trifluoroethyl group, etc. As the carbamoyl group which may be substituted by a lower alkyl group, there may be mentioned, for example, a carbamoyl group, a methylcarbamoyl group, a dimethylcarbamoyl group, a 1-pyrrolidinylcarbonyl group, etc. As the cycloalkyl group, there may be mentioned, for example, a cyclopropyl group, a cyclobutyl group, a cyclopentyl group, a cyclohexyl group, etc. The protective group and the eliminatable group in the carboxyl group which may be substituted by a protective group or an eliminatable group which is easily hydrolyzable in a human body have the same meanings as defined in the M previously mentioned. As the alkylene group having 3 to 4 carbon atoms, there may be mentioned, for example, a propylene group, a butylene group, etc.

Explanation of $R_4$ $R_4$ is a hydrogen atom or a lower alkyl group.

In the above, as the lower alkyl group, there may be mentioned a straight or branched alkyl group having 1 to 3 carbon atoms. For example, a methyl group, an ethyl group, an n- or iso-propyl group, etc. may be mentioned.

Explanation of A

A is a straight or branched lower alkylene group having 1 to 6 carbon atoms. As such alkylene groups, there may be mentioned, for example, a methylene group, an ethylene group, a trimethylene group, a tetramethylene group, a methylethylene group, an ethylethylene group, an ethylidene group, etc.

In the above formula (I), as the specific examples of the group represented by the following formula (a):

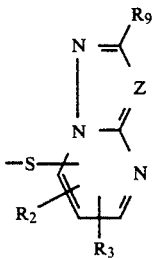

(b)

there may be mentioned, for example, the following groups.
(2-hydroxymethyl-s-triazolo[1,5-a]pyrimidin-7-yl)thio,
(2-hydroxymethyl-5-methyl-s-triazolo[1,5-a]pyrimidin-7-yl)thio,
(5-carboxy-2-hydroxymethyl-s-triazolo[1,5-a]pyrimidin-7-yl)thio,
(5-carbamoyl-2-hydroxymethyl-s-triazolo[1,5-a]pyrimidin-7-yl)thio,
(2-hydroxymethyl-5,6-dimethyl-s-triazolo[1,5-a]pyrimidin-7-yl)thio,
(2-hydroxymethyl-6,7-dihydro-5H-cyclopenta[d]-s-triazolo[1,5-a]pyrimidin-8-yl)thio,
(2-hydroxymethyl-5-trifluoromethyl-s-triazolo[1,5-a]pyrimidin-7-yl)thio,
(6-carboxy-2-hydroxymethyl-s-triazolo[1,5-a]pyrimidin-7-yl)thio,
(6-carbamoyl-2-hydroxymethyl-s-triazolo[1,5-a]pyrimidin-7-yl)thio,
(2-hydroxymethyl-5-monofluoromethyl-s-triazolo[1,5-a]pyrimidin-7-yl)thio,
(2-hydroxymethyl-5,6,7,8-tetrahydro-s-triazolo[5,1-b]quinazolin-9-yl)thio,
[2-(1-hydroxyethyl)-s-triazolo[1,5-a]pyrimidin-7-yl]thio,
[2-(1-hydroxyethyl)-5-methyl-s-triazolo[1,5-a]pyrimidin-7-yl]thio,
[5-carboxy-2-(1-hydroxyethyl)-s-triazolo[1,5-a]pyrimidin-7-yl]thio,
[5-carbamoyl-2-(1-hydroxyethyl)-s-triazolo[1,5-a]pyrimidin7-yl)thio,
[2-(1-hydroxyethyl)-5,6-dimethyl-s-triazolo[1,5-a]pyrimidin-7-yl]thio,
[2-(1-hydroxyethyl)-6,7-dihydro-5H-cyclopenta[d]-s-triazolo[1,5-a]pyrimidin-8-yl]thio,
[2-(1-hydroxyethyl)-5-trifluoromethyl-s-triazolo[1,5-a]pyrimidin-7-yl]thio,
[6-carboxy-2-(1-hydroxyethyl)-s-triazolo[1,5-a]pyrimidin-7-yl]thio,
[6-carbamoyl-2-(1-hydroxyethyl)-s-triazolo[1,5-a]pyrimidin7-yl)thio,
[2-(1-hydroxyethyl)-5-monofluoromethyl-s-triazolo[1,5-a]pyrimidin-7-yl]thio,
[2-(1-hydroxyethyl)-5,6,7,8-tetrahydro-s-triazolo[5,1-b]quinazolin-9-yl)thio,
[2-(2-hydroxyethyl)-s-triazolo[1,5-a]pyrimidin-7-yl]thio,
[2-(2-hydroxyethyl)-5-methyl-s-triazolo[1,5-a]pyrimidin-7-yl]thio,
[5-carboxy-2-(2-hydroxyethyl)-s-triazolo[1,5-a]pyrimidin-7-yl]thio,
[5-carbamoyl-2-(2-hydroxyethyl)-s-triazolo[1,5-a]pyrimidin7-yl)thio,
[2-(2-hydroxyethyl)-5,6-dimethyl-s-triazolo[1,5-a]pyrimidin-7-yl]thio,
[2-(2-hydroxyethyl)-6,7-dihydro-5H-cyclopenta[d]-s-triazolo[1,5-a]pyrimidin-8-yl]thio,
[2-(2-hydroxyethyl)-5-trifluoromethyl-s-triazolo[1,5-a]pyrimidin-7-yl]thio,
[6-carboxy-2-(2-hydroxyethyl)-s-triazolo[1,5-a]pyrimidin-7-yl]thio,
[6-carbamoyl-2-(2-hydroxyethyl)-s-triazolo[1,5-a]pyrimidin7-yl)thio,
[2-(2-hydroxyethyl)-5-monofluoromethyl-s-triazolo[1,5-a]pyrimidin-7-yl]thio,
[2-(2-hydroxyethyl)-5,6,7,8-tetrahydro-s-triazolo[5,1-b]quinazolin-9-yl)thio,
(2-methoxymethyl-s-triazolo[1,5-a]pyrimidin-7-yl)thio,
(2-methoxymethyl-5-methyl-s-triazolo[1,5-a]pyrimidin-7-yl)thio,
(5-carboxy-2-methoxymethyl-s-triazolo[1,5-a]pyrimidin-7-yl)thio,
(5-carbamoyl-2-methoxymethyl-s-triazolo[1,5-a]pyrimidin-7-yl)thio,
(2-methoxymethyl-5,6-dimethyl-s-triazolo[1,5-a]pyrimidin7-yl)thio,
(2-methoxymethyl-6,7-dihydro-5H-cyclopenta[d]-s-triazolo[1,5-a]pyrimidin-8-yl)thio,
(2-methoxymethyl-5-trifluoromethyl-s-triazolo[1,5-a]pyrimidin-7-yl)thio,
(6-carboxy-2-methoxymethyl-s-triazolo[1,5-a]pyrimidin-7-yl)thio,
(6-carbamoyl-2-methoxymethyl-s-triazolo[1,5-a]pyrimidin-7-yl)thio,
(2-methoxymethyl-5-monofluoromethyl-s-triazolo[1,5-a]pyrimidin-7-yl)thio,
(2-methoxymethyl-5,6,7,8-tetrahydro-s-triazolo[5,1-b]quinazolin-9-yl)thio,
(5-hydroxymethyl-2-methyl-s-triazolo[1,5-a]pyrimidin-7-yl)thio,
(2,5-bis(hydroxymethyl)-s-triazolo[1,5-a]pyrimidin-7-yl)thio,
(5-hydroxymethylpyrazolo[1,5-a]pyrimidin-7-yl)thio,
(3-hydroxymethyl-5-methylpyrazolo[1,5-a]pyrimidin-7-yl)thio,
(3-hydroxymethylpyrazolo[1,5-a]pyrimidin-7-yl)thio,
(5-hydroxymethyl-2-methylpyrazolo[1,5-a]pyrimidin-7-yl)thio,
(3-hydroxymethyl-5-methylpyrazolo[1,5-a]pyrimidin-7-yl)thio,
(3-carboxy-5-hydroxymethylpyrazolo[1,5-a]pyrimidin-7-yl)thio,
(3,5-bis(hydroxymethyl)pyrazolo[1,5-a]pyrimidin-7-yl)thio,
(5-methoxymethyl-2-methylpyrazolo[1,5-a]pyrimidin-7-yl)thio,
(5-methoxymethylpyrazolo[1,5-a]pyrimidin-7-yl)thio,
(7-hydroxymethyl-s-triazolo[1,5-a]pyrimidin-5-yl)thio,
(7-hydroxymethyl-2-methyl-s-triazolo[1,5-a]pyrimidin-5-yl)thio,
(7-hydroxymethyl-2-trifluoromethyl-s-triazolo[1,5-a]pyrimidin-5-yl)thio,
(2,7-bis(hydroxymethyl)-s-triazolo[1,5-a]pyrimidin-5-yl)thio,
(7-methoxymethyl-s-triazolo[1,5-a]pyrimidin-5-yl)thio,
(7-methoxymethyl-2-methyl-s-triazolo[1,5-a]pyrimidin-5-yl)thio,
(7-methoxymethyl-2-trifluoromethyl-s-triazolo[1,5-a]pyrimidin-5-yl)thio,
(7-hydroxymethyl-2-methoxymethyl-s-triazolo[1,5-a]pyrimidin-5-yl)thio,
(3-carboxy-7-hydroxymethylpyrazolo[1,5-a]pyrimidin-5-yl)thio, and (3-carboxy-7-methoxymethylpyrazolo[1,5-a]pyrimidin-5-yl)thio.

As the pharmaceutically acceptable salts of the β-lactam compounds according to the present invention, there may be mentioned alkali metal salts such as of sodium salts, potassium salts, etc.; alkaline earth metal salts such as of magnesium salts, calcium salts, etc.; ammonium salts; salts with organic bases such as of diisopropylamine, benzylamine, triethanolamine, triethylamine, N-methylmorpholine, pyridine, piperazine, etc.; salts with organic acids such as of acetic acid, formic acid, maleic acid, fumaric acid, methanesulfonic acid, p-toluenesulfonic acid, etc.; salts with inorganic acids such as of hydrochloric acid, hydrobromic acid, sulfuric acid, phosphoric acid and the like.

Manufacturing methods of the novel β-lactam compounds

The novel β-lactam compounds to be intended in the present invention can be synthesized according to the following four methods.

The first method

The title compound can be obtained by reacting the compound represented by the formula (II):

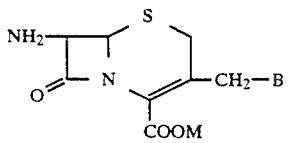

(II)

(wherein symbols in the formula are the same as mentioned above)
with the carboxylic acid represented by the formula (III):

$R_1$-OH    (III)

(wherein symbols in the formula are the same as mentioned above)
or its reactive derivative and then, if necessary, removing a protective group.

The second method

The compound represented by the formula (I'):

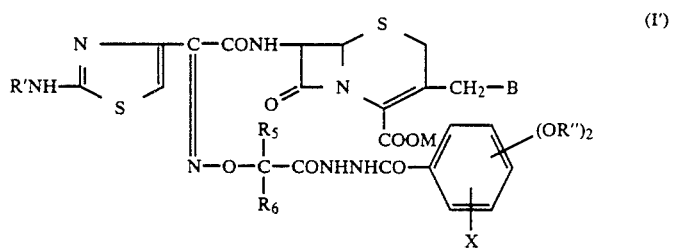

(I')

can be obtained by reacting the compound represented by the formula (IV):

(IV)

(wherein symbols in the formula are the same as mentioned above)
with the compound represented by the formula (V):

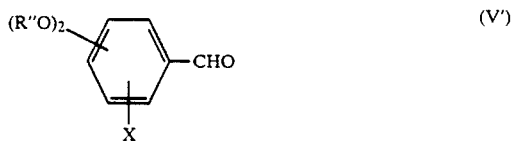

(V)

(wherein symbols in the formula are the same as mentioned above)
or its reactive derivative and then, if necessary, removing a protective group.

Also, the compound represented by the formula (I''):

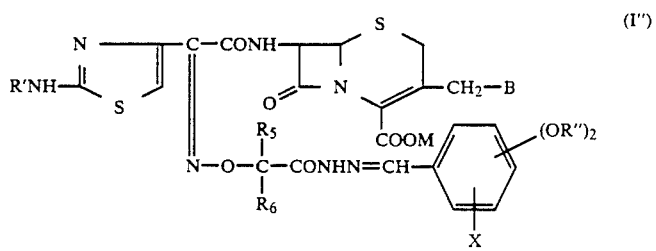

(I'')

(wherein symbols in the formula are the same as mentioned above)
can be obtained by reacting the above compound (IV) with the compound represented by the formula (V'):

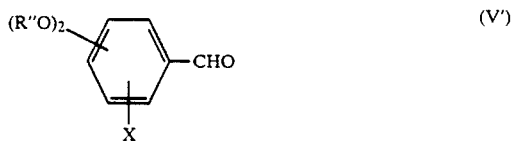

(V')

(wherein symbols in the formula are the same as mentioned above)
or its reactive derivative and then, if necessary, removing a protective group.

In this method, the starting compound represented by the formula (IV) is a novel compound, and an example of the synthesizing method is shown by referring reaction schemes in the following:

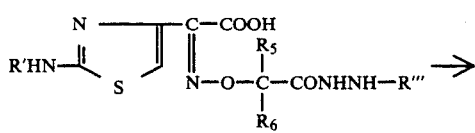
(IV)

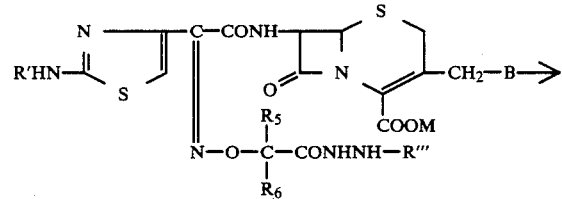

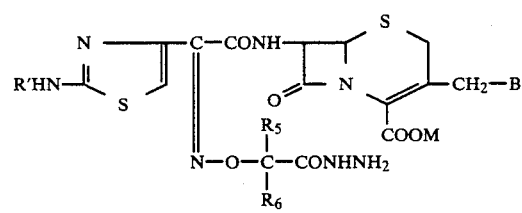

(wherein R''' is a protective group and the other symbols are the same as mentioned above).

The third method

The title compound can be obtained by reacting the compound represented by the formula (VI):

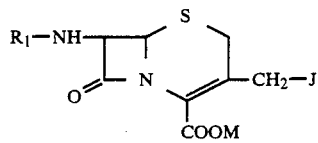
(VI)

wherein J represents a halogen atom or an acetoxy group and the other symbols are the same as mentioned above)
with the compound represented by the formula (VII):

B-H        (VII)

(wherein symbol in the formula is the same as mentioned above)
and then, if necessary, removing a protective group.

In this method, the starting compound represented by the formula (vII) is a novel compound, and an example of the synthesizing method is shown by referring reaction schemes in the following:

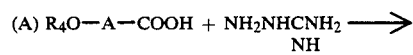

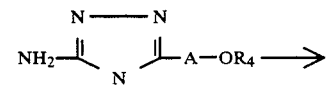

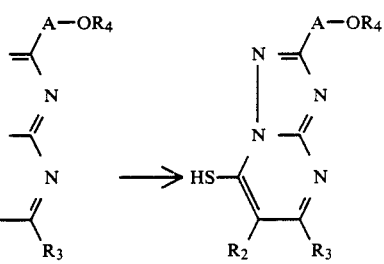
(VII'-a)

(wherein symbols in the formula are the same as mentioned above).

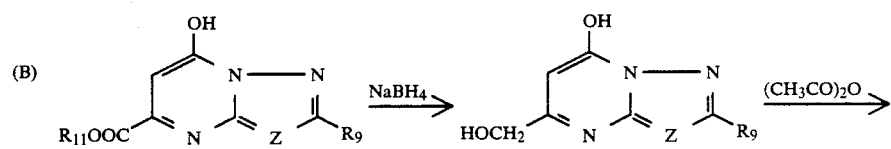

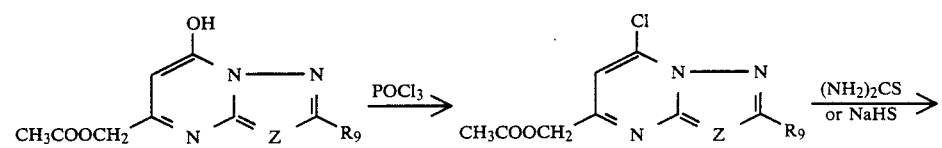

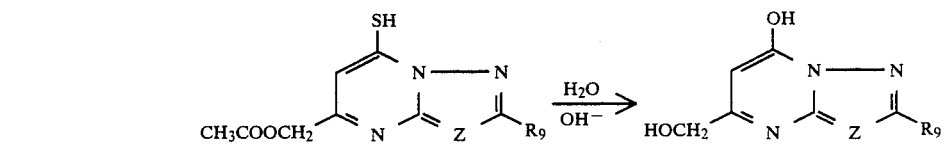
(VII'-b)

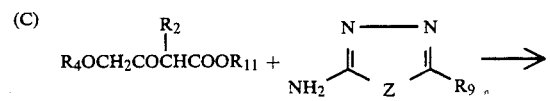

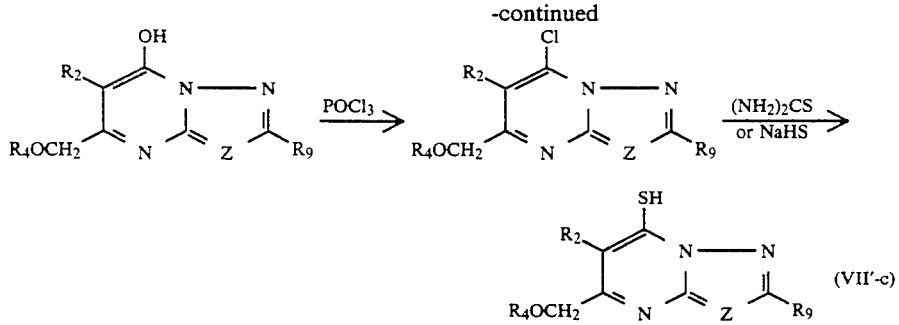 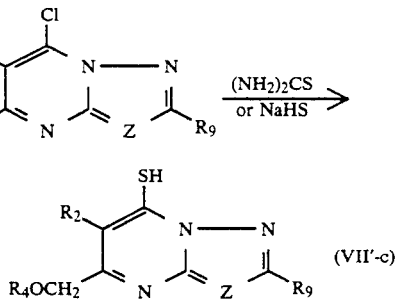

(wherein $R_{11}$ represents a lower alkyl group and the other symbols in the formulae are the same as mentioned above).

The fourth method

The compound represented by the formula (I'):

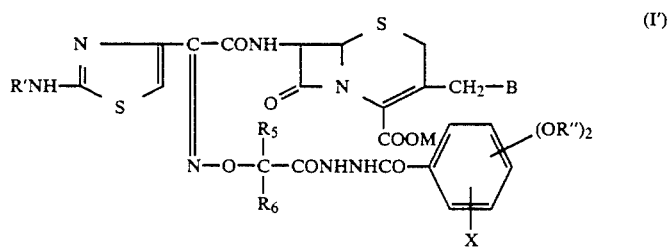

can be obtained by reacting the compound represented by the formula (VIII):

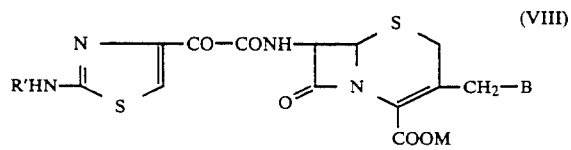

(wherein symbols in the formula are the same as mentioned above)
with the compound represented by the formula (IX):

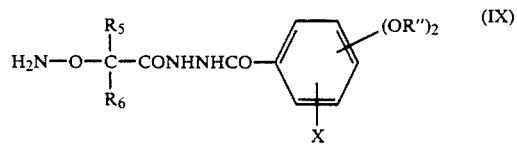

(wherein symbols in the formula are the same as mentioned above)
or a salt thereof, and removing a protective group, if necessary.

In the present reaction, it is preferred to use a salt of the compound of the formula (IX). As such a salt, there may preferably be used a salt with a mineral acid such as hydrochloric acid, or an organicc sulfonic acid such as p-toluenesulfonic acid. Such an acid is preferably used with an equimolar or a slight excess amount. The present reaction is preferably carried out in the presence of a polar solvent such as dimethylformamide, N-methylpyrrolidone, dimethylsulfoxide, acetonitrile or water, more preferably in dimethylacetamide. If the latter solvent is used, a syn-isomer of the final product can be obtained with particularly good yield. The temperature of the present reaction is preferably in the range of 0° C. to a room temperature.

In the following, producing methods of the novel β-lactam compounds according to the present invention will be explained in more detail.

The first method

Specific examples of the compound represented by the formula (III) may include, for example, the following compounds:

2-(2-Amino-1,3-thiazol-4-yl)-2-{1-[3-(3,4-dihydroxybenzoyl)carbazoyl]-1-methylethoxyimino}acetic acid,
2-(2-Amino-1,3-thiazol-4-yl)-2-{1-[3-(3,4-dihydroxybenzoyl)carbazoyl]ethoxyimino}acetic acid,
2-(2-Amino-1,3-thiazol-4-yl)-2-{[3-(3,4-dihydroxybenzoyl)carbazoyl]methoxyimino}acetic acid,
2-(2-Amino-1,3-thiazol-4-yl)-2-{1-[3-(3,4-diacetoxybenzoyl)carbazoyl]-1-methylethoxyimino}acetic acid,
2-(2-Amino-1,3-thiazol-4-yl)-2-{1-[3-(3,4-diacetoxybenzoyl)carbazoyl]ethoxyimino}acetic acid,
2-(2-Amino-1,3-thiazol-4-yl)-2-{[3-(3,4-diacetoxybenzoyl)carbazoyl]methoxyimino}acetic acid,
2-(2-Amino-1,3-thiazol-4-yl)acetic acid,
2-(2-Amino-1,3-thiazol-4-yl)-2-(hydroxyimino)acetic acid,
2-(2-Amino-1,3-thiazol-4-yl)-2-(methoxyimino)acetic acid,
2-(2-Thienyl)acetic acid.

The reaction between the compound (II) and the compound (III) is desirably carried out, in general, by using reactive derivatives of the compound (III) as the compound (III). In this case, it is desired to protect previously the hydroxyl group as an acyl ester. As the reactive derivatives, there may be mentioned, for example, acid halides, mixed acid anhydrides, active esters and the like. Further, while free carboxylic acids can be used as such, suitable condensation reagent may desirably be used in this case. As the reagent, there may be employed, for example, N,N'-dicyclohexylcarbodiimide (DCC), N,N'-carbonyldiimidazole, cyanuric chloride, Vilsmeier reagent and the like. Such reactions have been known in the field of penicillin chemistry, cephalosporin chemistry and peptide chemistry. The equimolar amounts of the compounds (II) and (III) are employed in general. These reactions are usually carried out at −10° to 30° C. for about 0.5 to 2 hours in a suitable solvent such as methylene chloride, chloroform, tetrahydrofuran, dioxane, dimethylformamide, dimethylacetamide, acetonitrile, acetone, water or mixed solvents of the above. Treatments after the reaction can be carried out by the methods well known in the art such as separation, purification and the like.

The second method

Specific examples of the compound represented by the formula (IV) may include, for example, the following compounds:

7-{2-[2-Amino-1,3-thiazol-4-yl]-2-(1-hydrazinocarbonyl-1-methylethoxyimino)acetamido}-3-[(2-hydroxymethyl-s-triazolo[1,5-a]pyrimidin-7-yl)thiomethyl-3-cephem-4-carboxylic acid 7-{2-[2-Amino-1,3-thiazol-4-yl]-2-(1-hydrazinocarbonyl-1-methylethoxyimino)acetamido}-3-[(2-hydroxymethyl-5-methyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-hydroxymethyl-5,6-dimethyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-hydroxymethyl-6,7-dihydro-5H-cyclopenta[d]-s-triazolo[1,5-a]pyrimidin-8-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-carboxy-2-hydroxymethyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-(1-hydroxyethyl)-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-(1-hydroxyethyl)-5-methyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-(1-hydroxyethyl)-5,6-dimethyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2-(1-hydroxyethyl)-6,7-dihydro-5H-cyclopenta[d]-s-triazolo[1,5-a]pyrimidin-8-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-carboxy-2-(1-hydroxyethyl)-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-hydroxymethyl-2-methyl-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2,5-bis(hydroxymethyl)-s-triazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-hydroxymethylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(3-hydroxymethyl-5-methylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(3-hydroxymethylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-hydroxymethyl-2-methylpyrazolo[1,5-a]pyrimidin-7-yl)thiomethyl]-3-cephem-4carboxylic acid, 7-{2-[2-Amino-1,3-thiazol-4-yl]-2-(1-hydrazinocarbonyl-1-methylethoxyimino)acetamido}-3-[(3-hydroxymethyl-5-methylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(3-carboxy-5-hydroxymethylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(3,5-bis(hydroxymethyl)pyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-methoxymethyl-2-methylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(5-methoxymethylpyrazolo[1,5-a]pyrimidin-7-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(7-hydroxymethyl-s-triazolo[1,5-a]pyrimidin-5-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(7-hydroxymethyl-2-methyl-s-triazolo[1,5-a]pyrimidin-5-yl)thiomethyl]-3-cephem-4carboxylic acid, 7-{2-[2-Amino-1,3-thiazol-4-yl]-2-(1-hydrazinocarbonyl-1-methylethoxyimino)acetamido}-3-[(7-hydroxymethyl-2-trifluoromethyl-s-triazolo[1,5-a]pyrimidin-5-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(2,7-bis(hydroxymethyl))-s-triazolo[1,5-a]pyrimidin-5-yl)thiomethyl]-3-cephem-4carboxylic acid, 7-{2-[2-Amino-1,3-thiazol-4-yl]-2-(1-hydrazinocarbonyl-1-methylethoxyimino)acetamido}-3-[(7-methoxymethyl-s-triazolo[1,5-a]pyrimidin-5-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(7-methoxymethyl-2-methyl-s-triazolo[1,5-a]pyrimidin-5-yl)thiomethyl]-3-cephem-4carboxylic acid, 7-{2-[2-Amino-1,3-thiazol-4-yl]-2-(1-hydrazinocarbonyl-1-methylethoxyimino)acetamido}-3-[(7-methoxymethyl-2-trifluoromethyl-s-triazolo[1,5-a]pyrimidin-5-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(7-hydroxymethyl-2-methoxymethyl-s-triazolo[1,5-a]pyrimidin-5-yl)thiomethyl]-3-cephem-4-carboxylic acid, 7-{2-[2-Amino-1,3-thiazol-4-yl]-2-(1-hydrazinocarbonyl-1-methylethoxyimino)acetamido}-3-[(3-carboxy-7- hydroxymethylpyrazolo[1,5-a]pyrimidin-5-yl)thiomethyl]-3-cephem-4-carboxylic acid, and
7-{2-[2-Amino-1,3-thiazol-4-yl]-2-(1-hydrazinocarbonyl-1-methylethoxyimino)acetamido}-3-[(3-carboxy-7-methoxymethylpyrazolo[1,5-a]pyrimidin-5-yl)thiomethyl]-3-cephem-4-carboxylic acid.

The reaction of the compound (IV) and the compound (V) is carried out by allowing the latter as such or the hydroxyl group protected as an acyl ester to react as acid halides, mixed acid anhydrides or active esters, or suitable condensation reagents such as N,N'-dicyclohexylcarbodiimide (DCC), N,N'-carbonyldiimidazole, cyanuric chloride, Vilsmeier reagent and the like can be employed. These reactions can be carried out in a suitable solvent such as methylene chloride, chloroform, tetrahydrofuran, dioxane, dimethylformamide, dimethylacetamide, actonitrile, acetone, water or mixed solvents of the above. at about $-10°$ to $50°$ C. for about 0.5 to 2 hours. The equimolar amounts of the starting compounds are employed in general.

The thus obtained compound (I) can be easily separated and purified by the known method.

The third method

Specific examples of the compound represented by the formula (VI) may include, for example, the following compounds:
7-{2-[2-Amino-1,3-thiazol-4-yl]-2-[1-(3-(3,4-dihydroxybenzoyl)carbazoyl)-1-methylethoxyimino]acetamido}-3-acetoxymethyl-3-cephem-4-carboxylic acid,
7-{2-[2-Amino-1,3-thiazol-4-yl]-2-[1-(3-(3,4-dihydroxybenzoyl)carbazoyl)ethoxyimino]acetamido}-3-acetoxymethyl3-cephem-4-carboxylic acid,
7-{2-[2-Amino-1,3-thiazol-4-yl]-2-[(3-(3,4-dihydroxybenzoyl)carbazoyl)methoxyimino]acetamido}-3-acetoxymethyl-3-cephem-4-carboxylic acid,
7-{2-[2-Amino-1,3-thiazol-4-yl]-2-[1-(3-(3,4-dihydroxybenzoyl)carbazoyl)-1-methylethoxyimino]acetamido}-3-chloromethyl-3-cephem-4-carboxylic acid,
7-55 2-[2-Amino-1,3-thiazol-4-yl]-2-[1-(3(3,4-dihydroxybenzoyl)carbazoyl)ethoxyimino]acetamido}-3-chloromethyl-3-cephem-4-carboxylic acid,
7-{2-[2-Amino-1,3-thiazol-4-yl]-2-[(3-(3,4-dihydroxybenzoyl)carbazoyl)methoxyimino]acetamido}-3-chloromethyl-3-cephem-4-carboxylic acid.

The compounds represented by the formula (VII) may include, for example, the following compounds:
2-Hydroxymethyl-7-mercapto-s-triazolo[1,5-a]pyrimidine, 2-Hydroxymethyl-7-mercapto-5-methyl-s-triazolo[1,5-a]pyrimidine,
5-Carboxy-2-hydroxymethyl-7-mercapto-s-triazolo[1,5-a]pyrimidine,
2-Hydroxymethyl-7-mercapto-5,6-dimethyl-s-triazolo[1,5-a]pyrimidine,
6-Carboxy-2-hydroxymethyl-7-mercapto-s-triazolo[1,5-a]pyrimidine,
2-Hydroxymethyl-5-monofluoromethyl-7-mercapto-s-triazolo1,5-a]pyrimidine,
2-Hydroxymethyl-6,7-dihydro-8-mercapto-5H-cyclopenta[d]-s-triazolo[1,5-a]pyrimidine,
2-Hydroxymethyl-5,6,7,8-tetrahydro-9-mercapto-s-triazolo5,1-b]quinazoline,
2-(1-Hydroxyethyl)-7-mercapto-s-triazolo[1,5-a]pyrimidine,
2-(1-Hydroxyethyl)-7-mercapto-5-methyl-s-triazolo[1,5-a]pyrimidine,
5-Carboxy-2-(1-hydroxyethyl)-7-mercapto-s-triazolo[1,5-a]pyrimidine,
2-(1-Hydroxyethyl)-7-mercapto-5,6-dimethyl-s-triazolo[1,5a]pyrimidine,
6-Carboxy-2-(1-hydroxyethyl)-7-mercapto-s-triazolo[1,5-a]pyrimidine,
2-(1-Hydroxyethyl)-5-monofluoromethyl-7-mercapto-s-triazolo[1,5-a]pyrimidine,
2-(1-Hydroxyethyl)-6,7-dihydro-8-mercapto-5H-cyclopenta[d]-s-triazolo[1,5-a]pyrimidine,
2-(1-Hydroxyethyl)-5,6,7,8-tetrahydro-9-mercapto-s-triazolo[5,1-b]quinazoline,
2-(2-Hydroxyethyl)-7-mercapto-s-triazolo[1,5-a]pyrimidine,
2-(2-Hydroxyethyl)-7-mercapto-5-methyl-s-triazolo[1,5-a]pyrimidine,
5-Carboxy-2-(2-hydroxyethyl)-7-mercapto-s-triazolo[1,5-a]pyrimidine,
2-(2-Hydroxyethyl)-7-mercapto-5,6-dimethyl-s-triazolo[1,5a]pyrimidine,
6-Carboxy-2-(2-hydroxyethyl)-7-mercapto-s-triazolo[1,5-a]pyrimidine,
2-(2-Hydroxyethyl)-5-monofluoromethyl-7-mercapto-s-triazolo[1,5-a]pyrimidine,
2-(2-Hydroxyethyl)-6,7-dihydro-8-mercapto-5H-cyclopenta[d]-s-triazolo[1,5-a]pyrimidine,
2-(2-Hydroxyethyl)-5,6,7,8-tetrahydro-9-mercapto-s-triazolo[5,1-b]quinazoline,
2-Methoxymethyl-7-mercapto-s-triazolo[1,5-a]pyrimidine,
-Methoxymethyl-7-mercapto-5-methyl-s-triazolo[1,5-a]pyrimidine,
5-Carboxy-2-methoxymethyl-7-mercapto-s-triazolo[1,5-a]pyrimidine,
2-Methoxymethyl-7-mercapto-5,6-dimethyl-s-triazolo[1,5-a]pyrimidine,
6-Carboxy-2-methoxymethyl-7-mercapto-s-triazolo[1,5-a]pyrimidine,
2-Methoxymethyl-5-monofluoromethyl-7-mercapto-s-triazolo-1,5-a]pyrimidine,
2-Methoxymethyl-6,7-dihydro-8-mercapto-5H-cyclopenta[d]-s-triazolo[1,5-a]pyrimidine,
2-Methoxymethyl-5,6,7,8-tetrahydro-9-mercapto-s-triazolo-5,1-b]quinazoline.
5-Hydroxymethyl-7-mercapto-2-methyl-s-triazolo[1,5-a]pyrimidine,
2,5-Bis(hydroxymethyl)-7-mercapto-s-triazolo[1,5-a]pyrimidine,
5-Methoxymethyl-7-mercapto-s-triazolo[1,5-a]pyrimidine,
5-Methoxymethyl-7-mercapto-2-methyl-s-triazolo[1,5-a]pyrimidine,
5-Methoxymethyl-7-mercapto-2-trifluoromethyl-s-triazolo-[1,5-a]pyrimidine,
2-Carboxy-5-methoxymethyl-7-mercapto-s-triazolo[1,5-a]-pyrimidine,
5-Hydroxymethyl-7-mercaptopyrazolo[1,5-a]pyrimidine,
3-Hydroxymethyl-7-mercapto-5-methylpyrazolo[1,5-a]pyrimidine,
3-Hydroxymethyl-7-mercaptopyrazolo[1,5-a]pyrimidine,
5-Hydroxymethyl-7-mercapto-2-methylpyrazolo[1,5-a]pyrimidine,
3-Hydroxymethyl-7-mercapto-5-methylpyrazolo[1,5-a]pyrimidine,
3-Carboxy-5-hydroxymethyl-7-mercaptopyrazolo[1,5-a]pyrimidine, 3,5-Bis(hydroxymethyl)-7-mercaptopyrazolo[1,5-a]pyrimidine,
7-Hydroxymethyl-5-mercapto-s-triazolo[1,5-a]pyrimidine,
7-Hydroxymethyl-5-mercapto-2-methyl-s-triazolo[1,5-a]pyrimidine,
7-Hydroxymethyl-5-mercapto-2-trifluoromethyl-s-triazolo-[1,5-a]pyrimidine,
2,7-Bis(hydroxymethyl)-5-mercapto-s-triazolo[1,5-a]pyrimidine,
5-Mercapto-7-methoxymethyl-s-triazolo[1,5-a]pyrimidine,
5-Mercapto-7-methoxymethyl-2-methyl-s-triazolo[1,5-a]pyrimidine,
5-Mercapto-7-methoxymethyl-2-trifluoromethyl-s-triazolo-[1,5-a]pyrimidine,
7-Hydroxymethyl-5-mercapto-2-methoxymethyl-s-triazolo-[1,5-a]pyrimidine,
3-Carboxy-7-hydroxymethyl-5-mercaptopyrazolo[1,5-a]pyrimidine and
3-Carboxy-5-mercapto-7-methoxymethylpyrazolo[1,5-a]pyrimidine.

The reaction of the compound (VI) and the compound (VII) is, when —COOM is a free carboxylic acid or its salt, carried out by contacting them in water or water and a water-soluble organic solvent such as acetone, methanol, ethanol, isopropanol, acetonitrile, etc. This reaction is desirably carried out at around neutral of pH and the reaction system can be maintained at around neutral by properly adding alkaline compounds such as an alkali hydroxide, an alkali carbonate, an alkali hydrogencarbonate, an alkali dihydrogenphosphate, an alkali monohydrogenphosphate, etc. The reaction is generally carried out at a temperature of about 20° to 70° C. The terminal point of the reaction is confirmed by a thin layer chromatography. The reaction time is about 0.5 to 24 hours. Since the thus obtained compound (I) is being dissolved as a water-soluble alkali salt in a reaction mixture, adsorption, separation and purification treatments are carried out by using adsorptive resins such as Diaion HP-20 (trade name, produced by Mitsubishi Chemical Industries, Ltd.), Amberlite XAD II (trade name, produced by Rohm & Haas, Co.) etc.

In case of -COOM being ester, the reaction is carried out in an organic solvent such as methanol, ethanol, isopropanol, tetrahydrofuran, acetonitrile, dimethylformamide and the like at 50° to 100° C. for 0.5 to 3 hours.

In the present method, equimolar amounts of the compound (VI) and the compound (VII) are generally employed, respectively.

Any protecting groups in an obtained compound, e.g. on phenolic hydroxy or amino, can be cleaved off; phenolic hydroxy protecting groups, e.g. as follows: acetyl with water at pH 7-8 or with ammonia, trimethylsilyl with ethanol or water, tetrahydropyranyl by acidic hydrolysis, e.g. with aqueous hydrochloric acid. Amino protecting groups can be cleaved off as follows: amino protecting groups which are cleavable by acid are preferably removed with the aid of a lower alkanecarboxylic acid which is optionally halogenated. In particular, formic acid or trifluoroacetic acid is used. As a rule, the temperature is room temperature, although slightly elevated or slightly lowered temperature can be used, e.g. in the range of about 0° C. to 40° C. protecting groups which are cleavable by alkali are generally hydrolyzed with dilute aqueous caustic alkali at 0° C. to 30° C. The chloroacetyl, bromoacetyl and iodoacetyl protecting groups can be cleaved off by means of thiourea in an acidic, neutral or alkaline medium at about 0°-30° C.

Any carboxy protecting groups can be cleaved off as follows: when the protecting group represents a trimethylsilyl group, this group can be removed especially readily by treatment with water or ethanol. Benzhydryl and t-butyl groups can be cleaved off with formic acid or trifluoroacetic acid in the manner given above. Allyl groups are removed, e.g. by means of palladium salts and tertiary amines such as N-methylpyrrolidine or N-methylmorpholine.

In the present invention, the compound (I) obtained by each methods of (1), (2), (3) and (4) as mentioned above can be converted into, if necessary, a pharmaceutically acceptable salt or an ester which is easily hydrolyzed in a human body when the compound has a free carboxylic acid.

For the manufacture of the readily hydrolyzable esters of the carboxylic acids of formula (I), the carboxylic acid is preferably with the iodide, containing the ester group. The reaction can be accelerated with the aid of a base, e.g. an alkali metal hydroxide or carbonate or an organic amine such as triethylamine. This reaction is preferably carried out in an inert organic solvent such as dimethylacetamide, hexamethylphosphoric acid triamide, dimethyl sulfoxide or, preferably, dimethylformamide. The temperature preferably lies in the range of about 0° to 40° C.

The manufacture of the salts and hydrates of the compounds of formula (I) or of the hydrates of these salts can be effected in a manner known per se, e.g. by reacting the carboxylic acid of formula (I) with an equivalent amount of the desired base, conventionally in a solvent such as water or in an organic solvent such as ethanol, methanol, acetone or many others. Corresponding salt formation is brought about by the addition of an organic or inorganic acid. The temperature of the salt formation is not critical. It generally lies at room temperature, but can also be slightly thereover or thereunder, for example, in the range of 0° C. to +50° C. The β-lactam compound according to the present invention can be administrated orally or non-orally to human beings or animals by various known administrating method.

Further, said compounds are used singly or by formulating with auxiliaries, liquid diluents, binders, lubricants, humectants, etc., which are pharmaceutically acceptable in general, for example, in the form of general medicinal compositions such as tablets, granulars, sugar coatings tablets, powders, capsules, gels, dry syrups, syrups, amples, suspensions, liquids, emulsions, ointments, pastes, creams, suppositories, etc.

Moreover, as the other additives which can be formulated, there may be mentioned dissolution delaying agents, adsorption accelerating agents, surface active agents, etc. Any way, any forms which are pharmaceutically acceptable can be employed.

The β-lactam compound according to the present invention can be used as alone or mixture of two or more different kinds of derivatives and the amount of the compounds is about 0.1 to 99.5 %, preferably 0.5 to 95 % based on the weight of the all medicinal composition.

The medicinal composition containing the compound of the present invention can be formulated with an other compounds which are pharmaceutically active as effective ingredients other than said compound or mixtures thereof.

A dosage per day to a patient of the novel β-lactam compound according to the present invention may be varied depending upon an individual man, kinds of animals, weights thereof and a state to be remedied, but generally is in the range of 1 to 1000 mg per 1 kg of weight, preferably about 10 to 800 mg.

According to the present invention, a novel β-lactam compound can be provided. The compound represented by the formula (I) of the present invention shows excellent antibacterial activity against a wide range of pathogenic bacteria such as gram negative bacteria and gram positive bacteria.

Accordingly, the β-lactam compound according to the present invention can be effectively utilized for the sake of prevention or remedy of diseases due to the aforesaid pathogenic bacteria in human beings or animals.

EXAMPLES

In the following, the present invention is explained in detail by referring to Examples.

EXAMPLE 1

Synthesis of 2-hydroxymethyl-7-mercapto-5-methyl-s-triazolo[1,5-a]pyrimidine (1) Synthesis of 3-amino-5-hydroxymethyl-s-triazole While stirring 1738 g (16 moles) of a 70 % glycolic acid, 1088 g (8 moles) of aminoguanidino-carboxylic acid was added thereto with little by little. To the mixture was added 8 ml of conc. nitric acid and the mixture was stirred under reflux for 24 hours. The reaction mixture was ice-cooled, and then precipitates were collected by filtration, washed with water and then dried.

Yield: 760 g $^1$H NMR (d6-DMSO) δ: 3.74 (s, 2H). (2) Synthesis of 7-hydroxy-2-hydroxymethyl-5-methyl-striazolo[1,5-a]pyrimidine After a mixture of 750 g of the compound obtained in (1), 3.5 iters of methyl acetoacetate and 75 ml of acetic acid was stirred at 100° C. for 24 hours, it was allowed to cool overnight and precipitated crystals were collected by filtration, washed with ethanol and dried.

Yield: 680 g $^1$H NMR (d6-DMSO) δ:
2.35 (s, 3H), 4.60 (s, 2H), 5.88 (s, 1H).

(3) Synthesis of 2-acetoxymethyl-7-hydroxy-5-methyl-striazolo[1,5-a]pyrimidine

A mixture of 520 g of the compound obtained in (2), 3 liters of DMF, 2 liters of acetic anhydride and 40 g of p-toluenesulfonic acid was stirred at 60° C. for 24 hours. The reaction mixture was condensed. To the residue precipitated crystals was added 4 liters of ether and the mixture was stirred, filtered and crystals obtained were dried.

Yield: 692 g

These crystals were recrystallized from 6 liters of methanol.

Yield: 297 g $^1$H NMR (d6-DMSO) δ:
2.17 (s, 3H), 2.38 (s, 3H), 5.27 (s, 2H), 5.95 (s, 1H).

(4) Synthesis of 2-acetoxymethyl-7-chloro-5-methyl-s-triazolo[1,5-a]pyrimidine

Phosphorus oxychloride (900 ml) was stirred under ice-cooling, and 200 ml of N,N-dimethylaniline was added dropwise thereto. To the mixture was added 173 g (0.78 mole) of the compound and the mixture was stirred at 55° to 60° C. for an hour. After removal of phosphorus oxychloride from the reaction mixture, the reaction mixture was dissolved in 2 liters of chloroform, and after adding crushed ice and water thereto, it was stirred. Subsequently, the reaction mixture was immediately transferred to a separating funnel, and a chloroform layer was obtained. The chloroform layer was washed three times with water and dried over anhydrous magnesium sulfate, and then condensed. To the residue crystallized was added one liter of isopropylether, rnd then the mixture was stirred and crystals were collected by filtration and dried.

Yield: 186 g $^1$H NMR (d6-DMSO) δ:
2.22 (s, 3H), 2.80 (s, 3H), 5.48 (s, 2H), 7.53 (s, 1H).

(5) Synthesis of 2-hydroxymethyl-7-mercapto-5-methyl-s-triazolo[1,5-a]pyrimidine In 400 ml of ethanol was dissolved 23.7 g of 2-acetoxymethyl-7-chloro-5-methyl-s-triazolo[1,5-a]pyrimidine, and 19 g of thiourea was added thereto and the mixture was stirred for 30 minutes under reflux. The reaction mixture was ice-cooled and the precipitated crystals were collected by filtration, washed with ethanol and dried. After the obtained crystals were dissolved in a 10 % potassium hydroxide aqueous solution and stirred for 30 minutes, pH was adjusted to 2 with addition of a 2N hydrochloric acid. The precipitated crystals were collected by filtration, washed with water and dried to obtain 15.3 g of the title compound.

$^1$H NMR (d6-DMSO) δ:
2.39 (s, 3H), 4.68 (s, 2H), 6.95 (s, 1H).

EXAMPLE 2

Synthesis of 7-amino-3-[(2-hydroxymethyl-5-methyl-s-triazolo[1,5-a]pyrimidin-7-yl)thiomethyl]-3-cephem-4-carboxylic acid In 130 ml of acetonitrile were suspended 11.08 g of 2-hydroxymethyl-7-mercapto-5-methyl-s-triazolo[1,5-a]pyrimidine and 15.38 g of 7-aminocephalosporanic acid, and 24.6 ml of boron trifluoride - ethyl ether complex was added thereto and the mixture was stirred at 50° C. for 2 hours. After the reaction mixture was ice-cooled, 300 ml of water was added thereto and pH thereof was adjusted to 2 with conc. aqueous ammonia. The precipitated crystals were collected by filtration, washed with water and with acetone, and then dried to obtain 18.5 of the title compound.

$^1$H NMR (CF$_3$COOD) δ:
2.93 (s, 3H), 3.93 (s, 2H), 4.88 (AB$_q$, 2H), 5.43 (s, 2H), 5.54 (s, 2H), 7.85 (s, 1H).

EXAMPLES 3 to 5

In the same manner as in Example 2, the following compounds were synthesized.

EXAMPLE 3

7-Amino-3-[(2-hydroxymethyl-s-triazolo[1,5-a]pyrimidin-7-yl)thiomethyl]-3-cephem-4-carboxylic acid $^1$H NMR (CF$_3$COOD) δ:
3.92 (s, 2H), 4.85 (AB$_q$, 2H), 5.38 (s, 2H), 5.51 (s, 2H), 7.97 (d, J=6Hz, 1H), 9.15 (d, J=6Hz, 1H).

EXAMPLE 4

7-Amino-3-[(2-hydroxymethyl-5,6-dimethyl-s-triazolo[1,5-a]-pyrimidin-7-yl)thiomethyl]-3-cephem-4-carboxylic acid

1H NMR (CF₃COOD) δ:

2.33 (s, 3H), 2.47 (s, 3H), 3.77 (s, 2H), 4.67 (AB$_q$, 2H), 5.36 (s, 2H), 5.48 (s, 2H).

EXAMPLE 5

7-Amino-3-[(2-hydroxymethyl-6,7-dihydro-5H-cyclopenta[d]-s-triazolo[1,5-a]pyrimidin-8-yl)thiomethyl]-3-cephem-4-carboxylic acid ¹H NMR (CF₃COOD)δ:
2.33 (s, 3H), 2.47 (s, 3H), 3.77 (s, 2H), 4.67 (AB$_q$, 2H), 5.36 (s, 2H), 5.48 (s, 2H).

EXAMPLE 6

Synthesis of diphenylmethyl 7-amino-3-[(2-hydroxymethyl-5-methyl-s-triazolo[1,5-a]pyrimidin-7-yl)thiomethyl]-3-cephem-4-carboxylate In a suspension of 17.48 g of 7-amino-3-[(2-hydroxymethyl5-methyl-s-triazolo[1,5-a]pyrimidin-7-yl)thiomethyl]-3-cephem-4-carboxylic acid in 100 ml of methanol and 300 ml of methylene chloride was added dropwise diphenyldiazomethane as 50 ml of a methylene chloride solution, synthesized from 23.55 g of benzophenonehydrazone, 26 g of mercuric oxide (yellow) and 200 ml of n-hexane while stirring, and the mixture was stirred at room temperature overnight. After the reaction mixture was condensed, ether was added thereto to effect crystallization. The crystals thus formed were collected by filtration and dried to obtain 30.15 g of the title compound. ¹H NMR (d₆-DMSO+CDCl₃) δ:
2.58 (s, 3H), 3.75 (bs, 2H), 4.33 (bs, 2H), 4.87 (s, 2H), 4.90 to 5.22 (m, 2H), 6.97 to 7.70 (m, 12H).

EXAMPLES 7 to 9

In the same manner as in Example 6, the following compounds were synthesized.

EXAMPLE 7

Diphenylmethyl 7-amino-3-[(2-hydroxymethyl-s-triazolo[1,5-a]pyrimidin-7-yl)thiomethyl]-3-cephem-4-carboxylate ¹H NMR (d₆-DMSO+CDCl₃) δ:
3.77 (s, 2H), 4.32 (bs, 2H), 4.84 (s, 2H), 4.92 to 5.26 (m, 2H), 6.95 to 7.78 (m, 12H), 8.85 (d, J=6Hz, 1H).

EXAMPLE 8

Diphenylmethyl 7-amino-3-[(2-hydroxymethyl-5,6-dimethyl-s-triazolo[1,5-a]pyrimidin-7-yl)thiomethyl]-3-cephem-4-carboxylate ¹H NMR (d₆-DMSO+CDCl₃) δ:
2.42 (s, 3H), 2.63 (s, 3H), 3.76 (s, 2H), 4.36 (bs, 2H), 4.88 (s, 2H), 4.88 to 5.23 (m, 2H), 6.87 to 7.68 (m, 11H).

EXAMPLE 9

Diphenylmethyl 7-amino-3-[(2-hydroxymethyl-6,7-dihydro-5H-cyclopenta[d]-s-triazolo[1,5-a]pyrimidin-8-yl)thiomethyl]3-cephem-4-carboxylate ¹H NMR (d₆-DMSO+CDCl₃) δ: 2.26 to 2.80 (m, 2H), 3.18 to 3.60 (m, 4H), 3.92 (s, 2H), 4.88 (AB$_q$, 2H), 5.44 (s, 2H), 5.53 (s, 2H).

EXAMPLE 10

Synthesis of 7-{2-[2-amino-1,3-thiazol-4-yl]-2-[1-(3-(3,4-dihydroxybenzoyl)carbazoyl)-1-methylethoxyimino]acetamido}3-[(2-hydroxymethyl-5-methyl-s-triazolo[1,5-a]pyrimidin-7-yl)thiomethyl]-3-cephem-4-carboxylic acid.hydrochloride In 40 ml of DMF were dissolved 6.44 g of 2-(2-amino-1,3-thiazol-4-yl)-2-{1-[3-(3,4-dihydroxybenzoyl)carbazoyl]-1-methylethoxyimino} acetic acid.hydrochloride, 12.2 g of diphenylmethyl 7-amino-3-[(2-hydroxymethyl-5-methyl-s-triazolo[1,5-a]pyrimidin-7-yl)thiomethyl]-3-cephem-4-carboxylate obtained in Example 6 and 2.6 g of 1-hydroxybenzotriazole, and the solution was ice-cooled. To the solution was added of 3.5 g of DCC, and the mixture was stirred for 15 minutes under ice-cooling and further stirred at room temperature for one hour. After the reaction mixture was filtered, 30 ml of chloroform was added to the filtrate and the mixture was added dropwise into 40 liters of ether. After precipitates were collected by filtration and washed with ether, a powder obtained by drying was purified through silica gel column to obtain powder. A mixed solution of 60 ml of trifluoroacetic acid and 15 ml of anisole was ice-cooled, and the powder obtained previously was added thereto, followed by stirring for 30 minutes. The resulting mixture was added dropwise into 500 ml of ether, and precipitates formed was collected by filtration, washed with ether and dried to obtain 7.82 g of the title compound.

¹H NMR (d₆-DMSO) δ: 1.60 (s, 6H), 2.62 (s, 3H), 3.80 (bs, 2H), 4.52 (bs, 2H), 4.70 (s, 2H), 5.32 (d, J=5Hz, 1H), 5.82 to 6.18 (m, 1H), 6.83 to 7.52 (m, 5H).

EXAMPLES 11 to 18

In the same manner as in Example 10, the following compounds were synthesized.

EXAMPLE 11

7-{2-[2-amino-1,3-thiazol-4-yl]-2-[1-(3-(3,4-dihydroxybenzoyl)carbazoyl)-1-methylethoxyimino]acetamido}-3-[(2-hydroxymethyl-s-triazolo[1,5-a]pyrimidin-7-yl)thiomethyl]-3-cephem-4-carboxylic acid.hydrochloride ¹H NMR (d₆-DMSO) δ: 1.59 (s, 6H), 3.78 (bs, 2H), 4.52 (bs, 2H), 4.68 (s, 2H), 5.35 (d, J=5Hz, 1H), 5.82 to 6.15 (m, 1H), 6.81 to 7.53 (m, 5H), 8.88 (d, J=5Hz, 1H).

Example 12

7-{2-[2-amino-1,3-thiazol-4-yl]-2-[1-(3-(3,4-dihydroxybenzoyl)carbazoyl)-1-methylethoxyimino]acetamido}-3-[(2-hydroxymethyl-5,6-dimethyl-s-triazolo[1,5-a]pyrimidin-7-yl)thiomethyl]-3-cephem-4-carboxylic acid.hydrochloride ¹H NMR (d₆-DMSO) δ: 1.60 (s, 6H), 2.51 (s, 3H), 2.62 (s, 3H), 3.78 (s, 2H), 4.48 (bs, 2H), 4.68 (s, 2H), 5.28 (d, J=4.5Hz, 1H), 5.78 to 6.20 (m, 1H), 6.82 to 7.60 (m, b 4H).

Example 13

7-{2-[2-amino-1,3-thiazol-4-yl]-2-[1-(3-(3,4-dihydroxybenzoyl)carbazoyl)-1-methylethoxyiminc]acetamido}-3-[(2-hydroxymethyl-6,7-dihydro-5H-cyclopenta[d]-s-triazolo[1,5-a]pyrimidin-8-yl)thiomethyl]-3-cephem-4-carboxylic acid.hydrochloride ¹H NMR (d₆-DMSO) δ: 1.62 (s, 6H), 2.02 to 2.50 (m, 2H), 2.90 to 3.44 (m, 4H), 3.81 (s, 2H), 4.48 (bs, 2H), 4.70 (s, 2H), 5.30 (d, J=5Hz, 1H), 5.80 to 6.14 (m, 1H), 6.83 to 7.66 (m, 4H).

Example 14

7-{2-[2-amino-1,3-thiazol-4-yl]-2-[1-(3-(3,4-dihydroxybenzoyl)carbazoyl)methylethoxyimino]acetamido}-3-[2-hydroxymethyl- 5-methyl-s-triazolo[1,5-a]pyrimidin- 7-yl)thiomethyl]-3-cephem-4-carboxylic acid.hydrochloride $^1$H NMR (d$_6$-DMSO) δ: 2.60 (s, 3H), 3.78 (s, 2H), 4.48 (bs, 2H), 4.66 (s, 2H), 5.28 (d, J=5Hz, 1H), 5.78 to 6.15 (m, 1H), 6.78 to 7.48 (m, 5H).

Example 15

7-{2-[2-amino-1,3-thiazol-4-yl]-2-[1-(3-(3,4-dihydroxybenzoyl)carbazoyl)ethoxyimino]acetamido}-3-[(2-hydroxymethyl-5-methyl-s-triazolo[1,5-a]pyrimidin-7-yl)thiomethyl]-3-cephem-4-carboxylic acid.hydrochloride $^1$H NMR (d$_6$-DMSO) δ: 1.50 (s, 3H), 2.62 (s, 3H), 3.77 (bs, 2H), 4.50 (bs, 2H), 4.68 to 4.83 (m, 3H), 5.22 (d, J=5Hz, 1H), 5.62 to 5.98 (m, 1H), 6.58 to 7.48 (m, 5H).

Example 16

7-[2-(2-amino-1,3-thiazol-4-yl)acetamido]-3-[(2-hydroxymethyl-5-methyl-s-triazolo[1,5-a]pyrimidin-7-yl)thiomethyl]-3-cephem-4-carboxylic acid.hydrochloride $^1$H NMR (d$_6$-DMSO) δ: 2.68 (s, 3H), 3.72 to 4.02 (m, 4H), 4.58 (bs, 2H), 4.70 (s, 2H), 5.38 (d, J=5Hz, 1H), 5.74 to 6.08 (m, 1H), 7.24 (s, 1H), 7.58 (s, 1H).

Example 17

7-[2-(2-amino-1,3-thiazol-4-yl)-2-(hydroxyimino)acetamido]3-[(2-hydroxymethyl-5-methyl-s-triazolo[1,5-a]pyrimidin-7-yl)thiomethyl]-3-cephem-4-carboxylic acid.hydrochloride $^1$H NMR (d$_6$-DMSO) δ: 2.63 (s, 3H), 3.82 (s, 2H), 4.58 (bs, 2H), 4.72 (s, 2H), 5.35 (d, J=4Hz, 1H), 5.74 to 6.06 (m, 1H), 7.23 (s, 1H), 7.62 (s, 1H).

Example 18

7-[2-(2-amino-1,3-thiazol-4-yl)-2-(methoxyimino)acetamido]-3-[(2-hydroxymethyl-5-methyl-s-triazolo[1,5-a]pyrimidin-7-yl)thiomethyl]-3-cephem-4-carboxylic acid.hydrochloride $^1$H NMR (d$_6$-DMSO) δ: 2.60 (s, 3H), 3.84 (s, 2H), 4.03 (s, 3H), 4.58 (bs, 1H), 4.70 (s, 2H), 5.37 (d, J=4Hz, 1H), 5.82 to 6.12 (m, 1H), 7.18 (s, 1H), 7.54 (s, 1H).

Example 19

Synthesis of 7-{2-[2-amino-1,3-thiazol-4-yl]-2-[1-(3-(3,4-dihydroxybenzoyl)carbazoyl)-1-methylethoxyimino]acetamide}-3-[(2-hydroxymethyl-5-methyl-s-triazolo[1,5-a]pyrimidin-7-yl)thiomethyl]-3-cephem-4-carboxylic acid.sodium salt In 200 ml of water was suspended 7.7 g of 7-{2-[2-amino-1,3-thiazol-4-yl]-2-[1-(3-(3,4-dihydroxybenzoyl)carbazoyl)-1-methylethoxyimino]acetamido}-3-[(2-hydroxymethyl-5-methyl-s-triazolo[1,5-a]pyrimidin-7-yl)thiomethyl]-3-cephem-4-carboxylic acid.hydrochloride, and a 5% sodium hydrogen carbonate solution was added thereto to dissolve at a pH 7. After the resulting solution was adsorbed to 500 ml of HP 20 column filled with water, it was washed with water. Subsequently, the mixture was eluted with a 50% methanol - water. After evaporation of methanol, the residue was freeze-dried to obtain 5.3 g of the title sodium salt compound.

Example 20

Synthesis of 7-[2-(2-thienyl)acetamido]-3-[(2-hydroxymethyl-5-methyl-s-triazolo[1,5-a]pyrimidin-7-yl)thiomethyl]-3-cephem-4-carboxylic acid In 100 ml of water was suspended 4.6 g of 7-amino-3-(2-hydroxymethyl-5-methyl-s-triazolo[1,5-a]pyrimidin-7-yl)thiomethyl]-3-cephem-4-carboxylic acid obtained in Example 2, and a 2N aqueous sodium hydroxide solution was added to the suspension and the mixture was dissolved at a pH 7. To this solution was while stirring under ice-cooling added dropwise a solution of 1.93 g of 2-thienyl acetyl chloride in 20 ml of ether over one hour. During this time, a pH of the mixture was maintained to 7 to 7.5 by addition of a 2N aqueous sodium hydroxide. After stirring for further one hour, the reaction mixture was washed with ethyl acetate. The reaction mixture was adjusted to pH 2.5 with a 2N hydrochloric acid under ice-cooling and stirring, and precipitated crystals were collected by filtration, washed with water and dried to obtain 4.81 g of the title compound.

$^1$H NMR (d$_6$-DMSO) δ: 2.65 (s, 3H), 3.68 to 4.04 (m, 4H), 4.54 (bs, 2H), 4.70 (s, 2H), 5.36 (d, J=5Hz, 1H), 5.68 to 6.12 (m, 1H), 7.08 to 7.28 (m, 3H), 7.50 to 7.70 (m, 1H).

Example 21

Synthesis of 7-[2-(2-amino-1,3-thiazol-4-yl)-2-(1-carboxy-methylethoxyimino)acetamido]-3-[(2-hydroxymethyl-5-methyl-s-triazolo[1,5-a]pyrimidin-7-yl)thiomethyl]-3-cephem-4-carboxylic acid In 150 ml of THF were dissolved 7.26 g of 2-(1-t-butoxycarbonyl-1-methylethoxyimino)-2-(2-tritylamino-1,3-thiazol-4-yl)acetic acid, 9.58 g of diphenylmethyl 7-amino-3-[(2-hydroxymethyl-5-s-triazolo[1,5-a]pyrimidin-7-yl)thiomethyl]-3-cephem-4-carboxylate obtained in Example 6 and 2.3 g of 1-hydroxybenzotriazole and the solution was ice-cooled. To the solution was added 3.09 g of DCC and the mixture was stirred under ice-cooling for 30 minutes, and further stirred at room temperature for 22 hours. After filtration of the reaction mixture, 300 ml of ethyl acetate was added to the filtrate, washed sucessively with a 2N hydrochloric acid, water, a 5% aqueous sodium hydrogen carbonate solution, water and a saturated saline solution, and dried over anhydrous magnesium sulfate. After evaporation of the solvent, the resulting oily product was purified through silica gel column to obtain 12 g of an oily product. This oily product was dissolved in 80 ml of anisole and the solution was ice-cooled. To the solution was added 80 ml of trifluoroacetic acid and the mixture was stirred at room temperature for 2.5 hours. The reaction mixture was added dropwise into 1.8 liters of ether, and precipitated material was collected by filtration and dried to obtain 4.5 g of the title compound.

$^1$H NMR (d6-DMSO) δ: 1.56 (s, 6H), 2.66 (s, 3H), 3.83 (bs, 2H), 4.54 (bs, 2H), 4.75 (s, 2H), 5.38 (d, J=5Hz, 1H), 5.81 to 6.14 (m, 1H), 7.18 (s, 1H), 7.45 (s, 1H).

Example 22

Synthesis of 7-mercapto-2-methoxymethyl-5-methyl-s-triazolo[1,5-a]pyrimidine (1) Synthesis of 7-hydroxy-2-methoxymethyl-5-methyl-s-triazolo[1,5-a]pyrimidine A mixture of 90 g of methoxy acetic acid, 68 g of aminoguanidine bicarbonate, 40 ml of water and 0.5 ml of conc. nitric acid was stirred under reflux for 24 hours, and then condensed. To the resulting residue were added 250 ml of methyl acetoacetate and 5 ml of acetic acid and the mixture was stirred in a bath of 100° to 120 ° C. After 4 hours, the mixture was cooled by allowing to stand and crystals were collected by filtration, washed with isopropanol and dried to obtain 82 g of the title compound.

$^1$H NMR (d$_6$-DMSO) δ: 2.40 (s, 3H), 3.43 (s, 3H), 4.57 (s, 2H), 5.92 (s, 1H).

(2) Synthesis of 7-chloro-2-methoxymethyl-5-methyl-s-triazolo[1,5-a]pyrimidine

To a mixed solution of 300 ml of phosphorus oxychloride and 50 ml of N,N-dimethylaniline was added 38.8 g of pyrimidine, and the mixture was stirred at 50° to 60° C. for one hour. After removing phosphorus oxychloride, the residue was dissolved in 500 ml of chloroform and stirred by adding ice. The chloroform layer was separated and washed with water, and then dried over anhydrous magnesium sulfate and distilled the solvent to obtain crystals. The crystals were collected by filtration and washed with water, and then dried to obtain the title compound.

$^1$H NMR (CDCl$_3$) δ: 2.76 (s, 3H), 3.62 (s, 3H), 4.85 (s, 2H), 7.25 (s, 1H).

(3) Synthesis of 7-mercapto-2-methoxymethyl-5-methyl-s-triazolo[1,5-a]pyrimidine In 350 ml of water was dissolved 24 g of sodium hydrosulfide and 34.5 g of 7-chloro-2-methoxymethyl-5-methyl-s-triazolo[1,5-a]pyrimidine was added thereto, and the mixture was stirred at 55° C. for one hour. After the reaction mixture was filtered, it was ice-cooled and adjusted to pH 1 with addition of a 2N-hydrochloric acid. The precipitates were collected by filtration, washed with water and with isopropanol, and dried to obtain 30.18 g of the title compound.

$^1$H NMR (d$_6$-DMSO) δ: 2.38 (s, 3H), 3.44 (s, 3H), 4.65 (s, 2H), 6.97 (s, 1H).

Example 23

Synthesis of 7-amino-3-[(2-methoxymethyl-5-methyl-s-triazolo[1,5-a]pyrimidin-7-yl)thiomethyl]-3-cephem-4-carboxylic acid In 600 ml of acetonitrile were suspended 30.1 g of 7-mercapto-2-methoxymethyl-5-methyl-s-triazolo[1,5-a]pyrimidine and 38.9 g of 7-aminocephalosporanic acid and 68.7 ml of boron trifluoride - ethyl ether complex was added thereto, and the mixture was stirred at room temperature for 6 hours. One liter of water was added to the reaction mixture and the mixture was adjusted to pH 2 with addition of a conc. aqueous ammonia. The precipitated crystals were collected by filtration, washed with water and with acetone, and then dried to obtain 30 g of the title compound.

$^1$H NMR (CF$_3$COOD) δ: 2.87 (s, 3H), 3.70 (s, 3H), 3.86 (s, 2H), 4.78 (AB$_q$, 2H), 5.24 to 5.68 (m, 4H).

Example 24

Synthesis of diphenylmethyl 7-amino-3-[(2-methoxymethyl-5-methyl-s-triazolo[1,5-a]pyrimidin-7-yl)thiomethyl]-3-cephem-4-carboxylate To a suspension comprising 30 g of 7-amino-3-[(2-methoxymethyl-5-methyl-s-triazolo[1,5-a]pyrimidin-7-yl)thiomethyl]-3-cephem-4-carboxylic acid, 170 ml of methanol and 510 ml of methylene chloride was added dropwise while stirring diphenyldiazomethane, which had been synthesized from 39.25 g of benzophenonehydrazone, 43.22 g of mercuric oxide (yellow) and 350 ml of n-hexane, in 50 ml of methylene chloride, and the mixture was stirred at room temperature overnight. After the reaction mixture was condensed and ether was added thereto to effect crystallization. The crystals were collected by filtration and dried, and the resulting powder was purified through silica gel column chromatography to obtain 31.1 g of the title compound.

$^1$H NMR (CDCl$_3$) δ: 2.52 (s, 3H), 3.56 (s, 3H), 3.69 (s, 2H), 4.25 (s, 2H), 4.72 to 5.08 (m, 4H), 6.70 (s, 1H), 7.04 (s, 1H), 7.17 to 7.63 (m, 10H).

Example 25

Synthesis of 7-{2-[2-amino-1,3-thiazol-4-yl]-2-[1-(3-(3,4-dihydroxybenzoyl)carbazoyl)-1-methylethoxyimino]acetamido}-3-[(2-methoxymethyl-5-methyl-s-triazolo[1,5-a]pyrimidin-7-yl)thiomethyl]-3-cephem-4-carboxylic acid.hydrochlride In 50 ml of DMF were dissolved 4.6 g of 2-(2-amino-1,3-thiazol-4-yl)-2-{1-[3-(3,4-dihydroxybenzoyl)carbazoyl]-1-methylethoxyimino} acetic acid.hydrochloride, 7.65 g of diphenylmethyl 7-amino-3-[(2-methoxymethyl-5-methyl-s-triazolo[1,5-a]pyrimidin-7-yl)thiomethyl]-3-cephem-4-carboxylate obtained in Example 24 and 1.84 g of 1-hydroxybenzotriazole, and the solution was ice-cooled. To the solution was added 2.5 g of DCC and the mixture was stirred for 15 minutes while ice-cooling and further stirred at room temperature for an hour. After the reaction mixture was filtered, 30 ml of chloroform was added to the filtrate and the mixture was added dropwise into 2 liters of ether. Precipitates were collected by filtration, washed with ether and then dried, and the powder thus obtained was purified through silica gel column chromatography to obtain powder.

A mixed solution of 20 ml of methylene chloride, 40 ml of trifluoroacetic acid and 10 ml of anisole was ice-cooled and the powder previously obtained was added to the solution, and the mixture was stirred for 30 minutes. Then, the mixture was added dropwise into 800 ml of ether, precipitates were collected by filtration, washed with ether and dried to obtain 5.9 g of the title compound.

$^1$H NMR (CDCl$_3$) δ: 1.60 (s, 6H), 2.65 (s, 3H), 3.45 (s, 3H), 3.88 (bs, 2H), 4.48 to 4.83 (m, 4H), 5.40 (d, J=5Hz, 1H), 5.88 to 6.24 (m, 1H), 6.82 to 7.68 (m, 5H).

Example 26

Synthesis of sodium 7-{2-[2-amino-1,3-thiazol-4-yl]-2-[1-(3-(3,4-dihydroxybenzoyl)carbazoyl)-1-methylethoxyimino]acetamido}-3-[(2-hydroxymethyl-5-meth.1-s-triazolo[1,5-a]pyrimidin-7-yl)thiomethyl]-3-cephem-4-carboxylate (1) Synthesis of 7-(2-amino-1,3-thiazol-4-ylglyoxylamido)- 3-[(2-hydroxymethyl-5-methyl-s-triazclo[1,5-a]pyrimidin-7-yl)thiomethyl]-3-cephem-4-carboxylic acid.hydrochloride To 20 ml of DMF was added 1.73 ml of phosphorus oxychloride and the mixture was stirred at 40° C. for 30 minutes. This mixture was cooled to −20° C. and 1.9 g of 2-(2-formylamino-1,3-thiazol-4-yl)glyoxylic acid, and the mixture was stirred at 0° C. for 3 hours.

After a mixed solution of 3.9 g of 7-amino-3-[(2-hydroxymethyl-5-methyl-s-triazolo[1,5-a]pyrimidin-7-yl)thiomethyl]-3-cephem-4-carboxylic acid, 7.5 ml of N,O-bis(trimethylsilyl)acetamide and 50 ml of methylene chloride was stirred at room temperature for 2 hours, the solution was cooled to −30° C. To the solution was added the previously obtained mixture, and the mixture was stirred at −30° C. for 2 hours. The reaction mixture was poured into 200 ml of ice-cold water and precipitated crystals were collected by filtration, washed with water and dried to obtain 1 g or powder.

Methanol (15 ml) was ice-cooled and 0.23 ml of phosphorus oxychloride was added thereto. Then, 1 g of the powder obtained above was added to the mixture and the mixture was stirred for 3 hours. The reaction mixture was added dropwise into 250 ml of ether, and precipitated crystals were collected by filtration, washed with water and dried to obtain 0.77 g of the title compound.

$^1$H NMR (d$_6$-DMSO) δ: 2.64 (s, 3H), 3.86 (bs, 2H), 4.62 (bs, 2H), 4.75 (s, 2H), 5.36 (d, J=5Hz, 1H), 5.72 to 6.12 (m, 1H), 7.45 (s, 1H), 8.40 (s, 1H).

(2) Synthesis of 7-{2-[2-amino-1,3-thiazol-4-yl]-2-[1-(3-(3,4-dihydroxybenzoyl)carbazoyl)-1-methylethoxyimino]acet- amido}-3-[(2-hydroxymethyl-5-methyl-s-triazolo[1,5-a]pyrimidin-7-yl)thiomethyl]-3-cephem-4-carboxylic acid.sodium salt In 10 ml of dimethylacetamide were dissolved 0.6 g of 7-(2-amino-1,3-thiazol-4-ylglyoxylamido)-3-[(2-hydroxymethyl-5-methyl-s-triazolo[1,5-a]pyrimidin-7-yl)thiomethyl]-3-cephem-4-carboxylic acid.hydrochloride and 0.54 g of 1-(2-aminoxy-2-methylpropionyl)-2-(3,4-dihydroxybenzoyl)hydrazine.hydrochloride and the mixture was stirred at room temperature for one day. The reaction mixture was condensed to a quarter and this was added dropwise in 30 ml of water. After pH was adjusted to 2, precipitating crystals were collected by filtration and washed with water, and then they were suspended in 20 ml of water and dissolved at pH 7 by adding a 5% sodium hydrogen carbonate solution. After this was adsorbed to a 50 ml of HP 20 column filled with water, this was eluted with a mixed solution of methanol and water, and then fractions containing the desired compound were condensed and freeze-dried to obtain 0.34 g of the title compound.

This has the same physical properties as those obtained in Example 19.

Example 27

Synthesis of sodium 7-[2-(2-amino-1,3-thiazol-4-yl)-2-methoxyiminoacetamido]-3-[(2-methoxymethyl-5-methyl-s-triazolo[1,5-a]pyrimidin-7-yl)thiomethyl-3-cephem-4-carboxylate In 50 ml of DMF were dissolved 2.29 g of 2-(2-formylamino-1,3-thiazol-4-yl)-2-methoxyiminoacetic acid, 7.65 g of diphenylmethyl 7-amino-3-[(2-methoxymethyl-5-methyl-s-triazolo[1,5-a]pyrimidin-7yl)thiomethyl]-3-cephem-4-carboxylate and 1.84 g of 1-hydroxybenzotriazole and the solution was ice-cooled. To the solution was added 2.5 g of DCC and the mixture was stirred for 15 minutes under ice-cooling and further stirred for one hour at room temperature. After filtration of the reaction mixture, 30 ml of chloroform was added to the filtrate and the mixture was added dropwise into 2 liters of ether, and precipitates were collected by filtration, washed with ether and dried to obtain powder.

To 80 ml of ice-cooled methanol was added dropwise 1.57 ml of phosphorus oxychloride, and the powder obtained above was added to the mixture and the mixture was stirred for 1.5 hours under ice-cooling. This reaction mixture was added dropwise into 1 liter of ether and precipitates were collected by filtration, washed with ether and then powder obtained by dryness was purified through silica gel column to obtain powder.

This powder was dissolved in 20 ml of methylene chloride, and 10 ml of anisole was added thereto and then 40 ml of trifluoroacetic acid was added thereto under ice-cooling and the mixture was stirred for 30 minutes. This mixture was added dropwise into 1 liter of ether and precipitates were collected by filtration, washed with ether and dried to obtain powder.

This powder was suspended in 100 ml of water, and dissolved by adding a 5% sodium hydrogen cabonate solution at pH 7. Then, this solution was adsorbed to a column of which 200 ml of HP 20 was filled with water, washed with water and then eluted with a methanol-water mixed solution. After condensing fractions containing the title compound, freeze-dried to obtain 2.96 g of the title compound.

$^1$H NMR (d$_6$-DMSO) δ: 2.60 (s, 3H), 3.41 (s, 3H), 3.78 (bs, 2H), 3.96 (s, 3H), 4.46 (bs, 2H), 4.63 (s, 2H), 5.25 (d, J=5Hz, 1H), 5.72 to 6.05 (m, 1H), 6.92 (s, 1H), 7.34 (s, 1H).

Example 28

Synthesis of 5-carboxy-2-hydroxymethyl-7-mercapto-s-triazolo[1,5-a]pyrimidine (1) Synthesis of 7-hydroxy-2-hydroxymethyl-5-methoxycarbonyl-s-triazolo[1,5-a]pyrimidine In 1.7 liters of methanol was suspended 60 g of 3-amino-5-hydroxymethyl-1,2,4-triazole and 75 ml of dimethyl acetylenedicarboxylate was added to the suspension, and the mixture was stirred at 30° C. for 20 hours. Precipitates were collected by filtration, washed with methanol and then dried to obtain 25.7 g of the title compound.

$^1$H NMR (d$_6$-DMSO) δ: 3.96 (s, 3H), 4.70 (s, 2H), 6.57 (s, 1H). (2) Synthesis of 2-acetoxymethyl-7-hydroxy-5-methoxycarbonyl-s-triazolo[1,5-a]pyrimidine A mixture of 25.7 g of 7-hydroxy-2-hydroxymethyl-5-methoxycarbonyl-s-triazolo[1,5-a]pyrimidine, 200 ml of DMF, 47 ml of acetic anhydride and 1 g of p-toluenesulfonic acid was stirred at 60° C. for 24 hours. The reaction mixture was condensed and 100 ml of methanol was added to the crystals precipitated residue, and the mixture was stirred. Then, crystals were collected by filtration, washed with methanol and dried to obtain 8.9 g of the title compound.

$^1$H NMR (d$_6$-DMSO) δ: 2.18 (s, 3H), 4.05 (s, 3H), 5.33 (s, 2H), 6.67 (s, 1H).

(3) Synthesis of 2-acetoxymethyl-7-chloro-5-methoxycarbonyl-s-triazolor[1,5-a]pyrimidine To a mixed solution of 30 ml of phosphorus oxychloride and 5.1 ml of N,N-dimethylaniline was added 5.32 g of 2-acetoxymethyl-7-hydroxy-5-methoxycarbonyl-s-triazolo[1,5-a]pyrimidine and the mixture was stirred at 50° C. for 1.5 hours, and then phosphorus oxychloride was removed. The residue was dissolved in 100 ml of chloroform and after addition of ice, the mixture was stirred. The chloroform layer was separated, washed with water and dried over anhydrous magnesium sulfate. The solvent was removed to obtain 5.75 g of the title compound as crystals.

$^1$H NMR (d$_6$-CDCl$_3$) δ: 2.25 (s, 3H), 4.18 (s, 3H), 5.58 (s, 2H), 8.20 (s, 1H).

(4) Synthesis of 5-carboxy-2-hydroxymethyl-7-mercapto-s-triazolo[1,5-a]pyrimidine In 200 ml of ethanol was dissolved 12 g of 2-acetoxymethyl-7-chloro-5-methoxycarbonyl-s-triazolo[1,5-a]pyrimidine under heating, and 8.36 g of thiourea was added to the solution and the mixture was stirred under reflux for 10 minutes. After cooling by allowed to stand, precipitates were collected by filteration, washed with ethanol and then dissolved in 100 ml of a 10% KOH, and the solution was stirred at room temperature for one hour. This solution was adjusted to pH 1 with 2N HCl under ice-cooling and stirring, and precipitates were collected by filtration, washed with water and then dried to obtain 8.13 g of the title compound.

$^1$H NMR (d$_6$-DMSO) δ: 4.86 (s, 2H), 7.67 (s, 1H).

Example 29

Synthesis of 7-amino-3-[(5-carboxy-2-hydroxymethyl-s-triazolo[1,5-a]pyrimidin-7-yl)thiomethyl]-3-cephem-4-carboxylic acid In 130 ml of acetonitrile were suspended 8 g of 5-carboxy-2-hydroxymethyl-7-mercapto-s-triazolo[1,5-a]pyrimidine and 9.53 g of 7-aminocephalosporanic acid and 17 ml of boron trifluoride - ethyl ether complex was added thereto, and the mixture was stirred at room temperature for 5 hours. To the reaction mixture was added 300 ml of water and the mixture was adjusted to pH 2 with conc. aqueous ammonia. Precipitated crystals were collected by filtration, washed with water and with acetone, and dried to obtain 10.1 g of the title compound.

$^1$H NMR (CF$_3$COOD) δ: 3.85 (s, 2H), 4.98 (broad s, 2H, 5.42 (broad s, 4H), 8.73 (s, 1H).

Example 30

Synthesis of diphenylmethyl 7-amino-3-[(5-carboxy-2-hydroxymethyl-s-triazolo[1,5-a]pyrimidin-7-yl)thiomethyl]-3-cephem-4-carboxylate To a suspension of 10 g of 7-amino-3-[(5-carboxy-2-hydroxymethyl-s-triazolo[1,5-a]pyrimidin-7yl)thiomethyl]-3-cephem-4-carboxylic acid, 100 ml of methanol and 300 ml of methylene chloride was added dropwise while stirring diphenyldiazomethane, which had been synthesized from 19.6 g of benzophenonehydrazone, 21.6 g of mercuric oxide (yellow) and 150 ml of n-hexane, in 30 ml of methylene chloride, and the mixture was stirred at room temperature overnight. After the reaction mixture was condensed and ether was added thereto to effect crystallization. The crystals were collected by filtration and dried to obtain 13.9 g of the title compound.

$^1$H NMR (CDCl$_3$) δ: 3.72 (broad s, 2H), 4.38 (broad s, 2H), 4.78 to 5.16 (m, 4H), 6.98 to 8.07 (m, 12H).

Example 31

Synthesis of 7-{2-[2-amino-1,3-thiazol-4-yl]-2-[1-(3-(3,4-dihydroxybenzoyl)carbazoyl)-1-methylethoxyimino]acetamido}-3-[(5-carboxy-2-hydroxymethyl-s-triazolo[1,5-a]pyrimidin-7-yl)thiomethyl]-3-cephem-4-carboxylic acid.hydrochloride In 40 ml of DMF were dissolved 3.22 g of 2-(2-amino-1,3-thiazol-4-yl)-2-{1-[3-(3,4-dihydroxybenzoyl)carbazoyl]-1-methylethoxyimino}acetic acid.hydrochloride, 6.5 g of diphenylmethyl 7-amino-3-[(5-carboxy-2-hydroxymethyl-s-triazolo[1,5-a]pyrimidin-7-yl)thiomethyl]-3-cephem-4-carboxylate and 1.27 g of 1-hydroxybenzotriazole, and the solution was ice-cooled. To the solution was added 1.73 g of DCC and the mixture was stirred for 15 minutes while ice-cooling and further stirred at room temperature for 45 minutes. After the reaction mixture was filtered, 20 ml of chloroform was added to the filtrate and the mixture was added dropwise into 2 liters of ether. Precipitates were collected by filtration, washed with ether and then dried, and the powder thus obtained was purified through silica gel column chromatography to obtain powder.

A mixed solution of 15 ml of methylene chloride, 30 ml of trifluoroacetic acid and 8 ml of anisole was ice-cooled and the powder previously obtained was added to the solution, and the mixture was stirred for 30 minutes. Then, the mixture was added dropwise into 500 ml of ether, precipitates were collected by filtration, washed with ether and dried to obtain 3.5 g of the title compound.

$^1$H NMR (d$_6$-DMSO) δ: 1.60 (s, 6H), 3.82 (bs, 2H), 4.63 to 4.97 (m, 4H), 5.33 (d, J=5Hz, 1H), 5.83 to 6.22 (m, 1H), 6.86 to 8.17 (m, 5H).

Example 32

Synthesis of sodium 7-[2-(2-amino-1,3-thiazol-4-yl)-2-methoxyiminoacetamido]-3-[(5-carboxy-2-hydroxymethyl-s-triazolo[1,5-a]pyrimidin-7-yl)thiomethyl-3-cephem-4-carboxylate In 40 ml of DMF were dissolved 1.6 g of 2-(2-formylamino-1,3-thiazol-4-yl)-2-methoxyiminoacetic acid, 6.5 g of diphenylmethyl 7-amino-3-[(5-carboxy-2-hydroxymethyl-s-triazolo[1,5-a]pyrimidin-7-yl)thiomethyl]-3-cephem-4-carboxylate and 1.29 g of 1-hydroxybenzotriazole and the solution was ice-cooled. To the solution was added 1.73 g of DCC and the mixture was stirred for 15 minutes under ice-cooling and further stirred for one hour at room temperature. After filtration of the reaction mixture, 20 ml of chloroform was added to the filtrate and the mixture was added dropwise into 2 liters of ether, and precipitates were collected by filtration, washed with ether and dried to obtain powder.

To 60 ml of ice-cooled methanol was added dropwise 1.1 ml of phosphorus oxychloride, and the powder obtained above was added to the mixture and the mixture was stirred for 1.5 hours under ice-cooling. This reaction mixture was added dropwise into 1 liter of ether and precipitates were collected by filtration, washed with ether and then powder obtained by dryness was purified through silica gel column to obtain powder.

This powder was added to a mixed solution of 10 ml of methylene chloride, 20 ml of trifluoroacetic acid and 5 ml of anisole, and the mixture was stirred for 30 minutes under ice-cooling. This mixture was added dropwise into 500 ml of ether and precipitates were collected by filtration, washed with ether and dried to obtain powder. This powder was suspended in 50 ml of water, and dissolved by adding a 5% sodium hydrogen cabonate solution at pH 6. Then, this solution was adsorbed to a column of which 150 ml of HP 20 was filled with water, washed with water and then eluted with a methanol-water mixed solution. After condensing fractions containing the title compound, freeze-dried to obtain 2.16 g of the title compound.

$^1$H NMR (d$_6$-DMSO) δ: 3.78 (s, 2H), 3.98 (s, 3H), 4.64 (bs, 2H), 4.81 (s, 2H), 5.30 (d, J=5Hz, 1H), 5.75 to 6.08 (m, 1H), 6.98 (s, 1H), 7.95 (s, 1H).

Example 33

Synthesis of diphenylmethyl 7-[2-(2-amino-1,3-thiazol-4-yl)-2-(1-carbazoyl-1-methylethoxyimino)acetamido]-3-[(2-hydroxymethyl-5-methyl-s-triazolo[1,5-a]pyrimidin-7-yl)thiomethyl]-3-cephem-4-carboxylate.hydrochloride In 50 ml of DMF were dissolved 3.43 g of 2-(2-formylamino-1,3-thiazol-4-yl)-2-[1-(3-formylcarbazoyl)-1-methylethoxyimino]acetic acid, 6.90 g of diphenylmethyl 7-amino-3-[(2-hydroxymethyl-5-methyl-s-triazolo[1,5-a]pyrimidin-7-yl)-thiomethyl]- 3-cephem-4-carboxylate and 1.84 g of 1-hydroxybenzotriazole and the solution was ice-cooled. To the solution was added 2.48 g of DCC, and the mixture was stirred under ice-cooling for 10 minutes and further stirred at room temperature for one hour. After filtration of the reaction mixture, 20 ml of chloroform was added to the filtrate and the mixture was added dropwise into 2 liters of ether. Precipitates were collected by filtration, washed with ether and dried to obtain powder. This powder was purified through a column filled with 100 g of silica gel (eluent: a mixed solution of methanol-chloroform) and obtained fractions containing the title compound was condensed, treated with ether and powdered. To 80 ml of ice-cooled methanol was added 1.74 ml of phosphorus oxychloride, and the powder previously obtained was added to the mixture and the mixture was stirred under ice-cooling for one hour. This reaction mixture was added dropwise into 2 liters of ether, and precipitates were collected by filtration, washed with ether and dried to obtain 6.05 g of the title compound.

$^1$H NMR (d$_6$-DMSO) δ: 1.62 (s, 6H), 2.61 (s, 3H), 3.92 (bs, 2H), 4.51 (bs, 2H), 4.80 (s, 2H), 5.48 (d, J=5Hz, 1H), 5.97 to 6.28 (m, 1H), 7.10 to 7.85 (m, 13H).

Example 34

Synthesis of sodium 7-{2-[2-amino-1,3-thiazol-4-yl]-2-[1-(3-(3,4-dihydroxybenzoyl)carbazoyl)-1-methylethoxyimino]acetamido}-3-[(2-hydroxymethyl-5-methyl-s-triazolo[1,5-a]pyrimidin-7-yl)thiomethyl]-3-cephem-4-carboxylate In 30 ml of methylene chloride was suspended 2.76 g of diphenylmethyl 7-[2-(2-amino-1,3-thiazol-4-yl)-2-(1-carbazoyl-1-methylethoxyimino)acetamido]-3-[(2-hydroxymethyl- 5-methyl-s-triazolo[1,5-a]pyrimidin-7-yl)thiomethyl]-3-cephem-4-carboxylate.dihydrochloride, and then 7.3 ml of N,O-bistrimethylsilylacetamide was added to the suspension and the mixture was stirred for 15 minutes. After ice-cooling of this mixture, 0.92 g of 3,4-diacetoxybenzoic acid chloride was added thereto and the mixture was stirred for 40 minutes. Thereafter, the mixture was added dropwise into one liter of ether and precipitates were collected by filtration and dried to obtain powder. After ice-cooling of a mixed solution of 25 ml of trifluoroacetic acid, 7 ml of anisole and 10 ml of methylene chloride, the powder previously obtained was added thereto and the mixture was stirred for 30 minutes. The mixture was added dropwise into 500 ml of ether and precipitates were collected by filtration and dried to obtain powder. The powder obtained was dissolved in 50 ml of methanol and 1 ml of a 25% aqueous ammonia solution was added thereto, and the mixture was stirred at room temperature for one hour. The reaction mixture was condensed and the residue obtained was dissolved in 50 ml of water. A pH of the solution was adjusted to 2 with a 2N hydrochloric acid and precipitated crystals were collected by filtration. These crystals were suspended in 50 ml of water and dissolved at pH 7 with addition of a 5% sodium hydrogen carbonate solution, and then adsorbed to a column filled with 100 ml of HP-20 and eluted with a mixed solution of methanol-water after washing with water. After collection of fractions containing the title compound and condensation, the residue was freeze-dried to obtain 0.9 g of the title compound.

$^1$H NMR (d$_6$-DMSO) δ: 1.59 (s, 6H), 2.60 (s, 3H), 3.80 (bs, 2H), 4.51 (bs, 2H), 4.70 (s, 2H), 5.33 (d, J=5Hz, 1H), 5.81 to 6.22 (m, 1H), 6.85 to 7.55 (m, 5H).

Example 35

Synthesis of 5-hydroxymethyl-7-mercapto-2-methyl-s-triazolo[1,5-a]pyrimidine (1) Synthesis of 7-hydroxy-5-methoxycarbonyl-2-methyl-s-triazolo[1,5-a]pyrimidine In a mixture of 114.5 ml of glacial acetic acid and 50 ml of water were added 136 g of aminoguanidine bicarbonate and 1 ml of conc. nitric acid and the mixture was refluxed for 24 hours. An oily produce obtained by removing water was dissolved in 800 ml of methanol, and 150 ml of dimethyl acetylenedicarboxylate was added dropwise thereto and the mixture was stirred at room temperature overnight. Precipitates were collected by filtration, washed with water and dried to obtain 58 g of the title compound.

$^1$H NMR (d$_6$-DMSO) δ: 2.18 (s, 3H), 3.76 (s, 3H), 6.61 (s, 1H).

(2) Synthesis of 7-hydroxy-5-hydroxymethyl-2-methyl-s-triazolo[1,5-a]pyrimidine

In 4 liters of ethanol was suspended 45.4 g of 7-hydroxy-5-methoxycarbonyl-2-methyl-s-triazolo[1,5-a]pyrimidine and 37.83 g of sodium borohydride was added little by little thereto, and the mixture was then stirred at room temperature for 3 hours. A residue obtained by removing ethanol was dissolved in 2 liters of water, and 500 ml of Amberlite IRC-50 (H$^+$) (trade name) was added thereto and stirred. Subsequently, the mixture was filtered and after removing water from the filtrate, 500 ml of methanol was added to the filtrate and the mixture was stirred. Then, methanol was removed from the mixture to obtain a residue. These procedures were repeated three times. Then, 500 ml of ethanol was added to the residue and the mixture was condensed. Precipitated crystals were collected by filtration, washed with ethanol and dried to obtain 39.35 g of the title compound.

$^1$H NMR (d$_6$-DMSO) δ: 2.26 (s, 3H), 4.32 (s, 2H), 5.78 (s, 1H).

(3) Synthesis of 5-acetoxymethyl-7-hydroxy-2-methyl-s-triazolo[1,5-a]pyrimidine

A mixture of 33.06 g of 7-hydroxy-5-hydroxymethyl-2-methyl-s-triazolo[1,5-a]pyrimidine, 500 ml of DMF, 86 ml of anhydrous acetic acid and 1.5 g of p-toluenesulfonic acid was stirred in a bath at 50° C. for 6 hours. To an oily residue obtained by removing DMF was added 300 ml of isopropanol to dissolve therein, and the solution was added dropwise in 4 liters of ether. Precipitates were collected by filtration and dried to obtain 38.08 g of the title compound.

$^1$H NMR (d$_6$-DMSO) δ: 2.26 (s, 3H), 2.50 (s, 3H), 5.16 (s, 2H), 6.14 (s, 1H).

(4) Synthesis of 5-acetoxymethyl-7-chloro-2-methyl-s-triazolo[1,5-a]pyrimidine

In 300 ml of phosphorus oxychloride was added dropwise 40 ml of N,N-dimethylaniline, and 35 g of 5-acetoxymethyl-7-hydroxy-2-methyl-s-triazolo[1,5-a]pyrimidine was added to the mixture and the mixture was stirred at 50° C. for one hour. An oily residue obtained by removing phosphorus oxychloride was dissolved in 500 ml of chloroform and ice-cooled. After addition of crushed ice and water to the mixture and stirring thereof, a chloroform layer was separated, washed with water and dried over anhydrous magnesium sulfate. Then, removing a solvent, an oily product was obtained. This was applied to a silica gel column chromatography (eluent: chloroform) and fractions containing the title compound were condensed to obtain an oily product. This was allowed to stand to cool and crystallized to obtain 31 g of the title compound.

$^1$H NMR (d$_6$-CDCl$_3$) 67 : 2.23 (s, 3H), 2.66 (s, 3H), 5.35 (s, 2H), 7.36 (s, 1H).

(5) Synthesis of 5-hydroxymethyl-7-mercapto-2-methyl-s-triazolo[1,5-a]pyrimidine In 600 ml of ethanol was dissolved 31 g of 5-acetoxymethyl-7-chloro-2-methyl-s-triazolo[1,5-a]pyrimidine, and 29.5 g of thiourea was added thereto and the mixture was refluxed for 10 minutes. The reaction mixture was ice-cooled and resulting precipitated crystal was collected by filtration. The crystal was dissolved in 600 ml of a 5% potassium hydroxide and the mixture was stirred for 30 minutes, ice-cooled and adjusted to pH 2 with 2N hydrochloric acid. Precipitated crystal was collected by filtration, washed with water and dried to obtain 16.33 g of the title compound.

$^1$H NMR (d$_6$-DMSO) δ: 2.58 (s, 3H), 4.57 (s, 2H), 7.21 (s, 1H).

Example 36

Synthesis of 7-amino-3-[(5-hydroxymethyl-2-methyl-s-triazolo[1,5-a]pyrimidin-7-yl)thiomethyl]-3-cephem-4-carboxylic acid In 120 ml of acetonitrile were suspended 9.8 g of 5-hydroxymethyl-7-mercapto-2-methyl-s-triazolo[1,5-a]pyrimidine and 13.6 g of 7-aminocephalosporanic acid, and 22 ml of boron trifluoride-ethyl ether complex was added to the suspension and the mixture was stirred at 50° C. for 3 hours. After cooling the reaction mixture, 250 ml of water was added thereto and the mixture was adjusted to pH 2 with conc. aqueous ammonia precipitated crystal was collected by filtration, washed with water, washed with acetone and then dried to obtain 11.6 g of the title compound.

$^1$H NMR (CF3COOD) δ: 2.86 (s, 3H), 3.88 (s, 2H), 5.04 (broad s, 2H), 5.34 (s, 2H), 5.60 (s, 2H), 8.24 (s, 1H).

Example 37

Synthesis of diphenylmethyl 7-amino-3-[(5-hydroxymethyl-2-methyl-s-triazolo[1,5-a]pyrimidin-7-yl)thiomethyl]-3-cephem-4-carboxylate In a suspension of 11.6 g of 7-amino-3-[(5-hydroxymethyl-2-methyl-s-triazolo[1,5-a]pyrimidin-7-yl)thiomethyl]-3-cephem-4-carboxylic acid, 70 ml of methanol and 200 ml of methylene chloride was added dropwise, while stirring, diphenyldiazomethane synthesized from 15.7 g of benzophenonehydrazone, 17.3 g of mercuric oxide (yellow) and 130 ml of n-hexane, in 50 ml of methylene chloride solution, and the mixture was stirred at room temperature overnight. After the reaction mixture was condensed, ether was added thereto to crystalize, and crystal was collected by filtration and dried to obtain 15.9 g of the title compound.

$^1$H NMR (d$_6$-DMSO+CDCl$_3$) δ: 2.57 (s, 3H), 3.74 (broad s, 2H), 4.36 (broad s, 2H), 4.77 (s, 2H), 4.93 to 5.22 (m, 2H), 7.04 to 7.78 (m, 12H).

Example 38

Synthesis of sodium 7-{2-[2-amino-1,3-thiazol-4-yl]-2-[1-(3-(3,4-dihydroxybenzoyl)carbazoyl)-1-methylethoxyimino]acetamido}-3-[(5-hydroxymethyl-2-methyl-s-triazolo[1,5-a]pyrimidin-7-yl)thiomethyl]-3-cephem-4-carboxylate In 30 ml of DMF were dissolved 3.22 g of 2-(2-amino-1,3-thiazol-4-yl)-2-{1-[3-(3,4-dihydroxybenzoyl)carbazoyl]-1-methylethoxyimino}acetic acid.hydrochloride, 5.17 g of diphenylmethyl 7-amino-3-[(5-hydroxymethyl-2-methyl-s-triazolo[1,5-a]pyrimidin-7-yl)thiomethyl]-3-cephem-4-carboxylate obtained in Example 37 and 1.38 g of 1-hydroxybenzotriazole and ice-cooled. Then, 1.86 g of DCC was added thereto and the mixture was stirred for 15 minutes under ice-cooling, and further stirred at room temperature for 30 minutes. After the reaction mixture was filtered, 15 ml of chloroform was added thereto and the mixture was added dropwise into 4 liters of ether. precipitates were collected by filtration, washed with ether and then dried. Powder obtained was purified through silica gel column chromatography to obtain powder. A mixed solution of 30 ml of trifluoroacetic acid and 8 ml of anisole was ice-cooled and the powder previously obtained was added thereto, and the mixture was stirred for 30 minutes and added dropwise into 400 ml of ether, precipitates were collected by filtration, washed with ether and then dried to obtain powder. The powder was suspended in 200 ml of water and dissolved at pH 7 by adding a 5% sodium hydrogencarbonate solution. After the resulting solution was adsorbed to 200 ml of HP 20 column filled with water, it was washed with water Subsequently, the mixture was eluted with a 50% methanol-water After evaporation of methanol, the residue was freeze-dried to obtain 3.75 g of the title compound.

$^1$H NMR (d$_6$-DMSO) δ: 1.60 (s, 6H), 2.55 (s, 3H), 3.82 (broad s, 2H), 4.54 (broad s, 2H), 4.73 (s, 2H), 5.38 (d, J=5 Hz, 1H), 5.92 to 6.26 (m, 1H), 6.80 to 7.23 (m, 5H).

Example 39

Synthesis of sodium 7-[2-(2-amino-1,3-thiazol-4-yl)-2-methoxyimino)acetamido]-3-[(5-hydroxymethyl-2-methyl-s-triazolo[1,5-a]pyrimidin-7-yl)thiomethyl]-3-cephem-4-carboxylate In 30 ml of DMF were dissolved 1.6 g of 2-(2-formylamino-1,3-thiazol-4-yl)-2-methoxyiminoacetic acid, 5.17 g of diphenylmethyl 7-amino-3-[(5-hydroxymethyl-2-methyl-s-triazolo[1,5-a]pyrimidin-7-yl)thiomethyl]-3-cephem-4-carboxylate and 1.38 g of 1-hydroxybenzotriazole and ice-cooled. Then, 1.86 g of DCC was added thereto and the mixture was stirred for 15 minutes under ice-cooling, and further stirred at room temperature for one hour. After the reaction mixture was filtered, 15 ml of chloroform was added to the filtrate and the mixture was added dropwise into 2 liters of ether. Precipitates were collected by filtration, washed with ether and then dried. To an ice-cooled 60 ml of methanol was added dropwise 1.45 ml of phosphorus oxychloride, and to the mixture was added the powder previously obtained, and the mixture was stirred for one hour under ice-cooling. The reaction mixture was added dropwise into 800 ml of ether and precipitates were collected by filtration, washed with ether and then dried to obtain powder. The powder was purified through silica gel column chromatography to obtain a powder. The powder was added to a mixed solution of 30 ml of trifluoroacetic acid and 8 ml of anisole and the mixture was stirred for 30 minutes under ice-cooling. The resulting mixture was added dropwise into 400 ml of ether, and precipitates were collected by filtration, washed with ether and dried to obtain a powder. After this powder was suspended in 50 ml of water and dissolved at pH 6 by addition of a 5% sodium hydrogencarbonate solution, it was adsorbed to 100 ml of HP 20 column filled with water and then washed with water. Subsequently, the mixture was eluted with a methanol-water mixed solution. After condensation of fractions containing the title compound, the residue was freeze-dried to obtain 3.0 g of the title compound.

$^1$H NMR (d$_6$-DMSO) δ: 2.62 (s, 3H), 3.88 (broad s, 2H), 4.10 (s, 3H), 4.68 (broad s, 2H), 4.79 (s, 2H), 5.40 (d, J=5 Hz, 1H), 5.79 to 6.14 (m, 1H), 7.18 (s, 1H), 7.77 (s, 1H).

Example 40

Synthesis of 2,5-bis(hydroxymethyl)-7-mercapto-s-triazolo[1,5-a]pyrimidine (1) Synthesis of 7-hydroxy-2,5-bis(hydroxymethyl)-s-triazolo[1,5-a]pyrimidine In 4 liters of ethanol was suspended 48.94 g of 7-hydroxy-2-hydroxymethyl-5-methoxycarbonyl-s-triazolo[1,5-a]pyrimidine, and 33 g of sodium borohydride was added little by little thereto and then the mixture was stirred at room temperature for 3 hours and then refluxed for 4 hours. A residue obtained by removing ethanol was dissolved in 2 liters of water, and 500 ml of Amberlite IRC-50 (H+) (trade name) was added thereto and stirred. Subsequently, the mixture was filtered and after removing water from the filtrate, 500 ml of methanol was added to the filtrate and the mixture was stirred. Then, methanol was removed from the mixture to obtain a residue. These procedures were repeated three times. Then, 500 ml of ethanol was added to the residue and the mixture was condensed. Precipitated crystal was collected by filtration, washed with ethanol and dried to obtain 39.35 g of the title compound.

$^1$H NMR (d$_6$-DMSO) δ: 4.53 (s, 2H), 4.62 (s, 2H), 6.11 (s, 1H).

(2) Synthesis of 2,5-bis(acetoxymethyl)-7-hydroxy-2-methyl-s-triazolo[1,5-a]pyrimidine A mixture of 34.96 g of 7-hydroxy-2,5-bis(hydroxymethyl)-s-triazolo[1,5-a]pyrimidine, 850 ml of DMF, 120 ml of anhydrous acetic acid and 3.42 g of p-toluenesulfonic acid was stirred in a bath at 50° C. for 2 hours. To an oily residue obtained by removing DMF was added 250 ml of ethanol to dissolve therein, and the solution was added dropwise in 4 liters of ether. Precipitates were collected by filtration and dried to obtain 30.57 g of the title compound.

$^1$H NMR (d$_6$-DMSO) δ: 2.11 (s, 3H), 2.17 (s, 3H), 4.98 (s, 2H), 5.17 (s, 2H), 5.80 (s, 1H).

(3) Synthesis of 7-chloro-2,5-bis(acetoxymethyl)-s-triazolo[1,5-a]pyrimidine

In 300 ml of phosphorus oxychloride was added dropwise 28 ml of N,N-dimethylaniline, and 30.5 g of 2,5-bis(acetoxymethyl)-7-hydroxy-s-triazolo[1,5-a]pyrimidine was added to the mixture and the mixture was stirred at 50° C. for 1.5 hours. An oily residue obtained by removing phosphorus oxychloride was dissolved in 500 ml of chloroform and ice-cooled. After addition of crushed ice and water to the mixture and stirring thereof, a chloroform layer was separated, washed with water and dried over anhydrous magnesium sulfate. Then, the mixture was condensed. This was applied to a silica gel column chromatography (eluent: chloroform) and fractions containing the title compound were condensed to obtain 14 g of the title compound as an oily product.

$^1$H NMR (d$_6$-CDCl$_3$) δ: 2.35 (s, 3H), 2.31 (s, 3H), 5.44 (s, 2H), 5.52 (s, 2H), 7.44 (s, 1H).

(4) Synthesis of 2,5-bis(hydroxymethyl)-7-mercapto-s-triazolo[1,5-a]pyrimidine

In 300 ml of ethanol was dissolved 14 g of 7-chloro-2,5-bis(acetoxymethyl)-s-triazolo[1,5-a]pyrimidine, and 10.7 g of thiourea was added thereto and the mixture was refluxed for 10 minutes. After removing ethanol from the reaction mixture, the residue was dissolved in 230 ml of a 5% potassium hydroxide. The mixture was stirred for 30 minutes, ice-cooled and adjusted to pH 2 with 2N hydrochloric acid. precipitated crystal was collected by filtration, washed with water and dried to obtain 7.16 g of the title compound.

$^1$H NMR (d$_6$-DMSO) δ: 4.58 (s, 2H), 4.77 (s, 2H), 7.19 (s, 1H).

Example 41

Synthesis of 7-amino-3-[(2,5-bis(hydroxymethyl)-s-triazolo[1,5-a]pyrimidin-7-yl)thiomethyl]-3-cephem-4-carboxylic acid In 80 ml of acetonitrile were suspended 7.1 g of 2,5-bis(hydroxymethyl)-7-mercapto-s-triazolo[1,5-a]pyrimidine and 9.1 g of 7-aminocephalosporanic acid, and 15 ml of boron trifluoride-ethyl ether complex was added to the suspension and the mixture was stirred at 50° C. for 3 hours. After cooling the reaction mixture, 200 ml of water was added thereto and the mixture was adjusted to pH 2 with conc. aqueous ammonia. Precipitated crystal was collected by filtration, washed with water, washed with acetone and then dried to obtain 5.34 g of the title compound.

$^1$H NMR (CF$_3$COOD) δ: 3.97 (s, 2H), 4.98 (broad s, 2H), 5.29 (s, 2H), 5.46 (s, 2H), 5.54 (s, 2H), 8.26 (s, 1H).

Example 42

Synthesis of diphenylmethyl 7-amino-3-[(2,5-bis(hydroxymethyl)-s-triazolo[1,5-a]pyrimidin-7-yl)thiomethyl]-3-cephem-4-carboxylate In a suspension of 5.3 g of 7-amino-3-[(2,5-bis(hydroxymethyl)-s-triazolo[1,5-a]pyrimidin-7-yl)thiomethyl]-3-cephem-4-carboxylic acid, 35 ml of methanol and 100 ml of methylene chloride was added dropwise, while stirring, diphenyldiazomethane synthesized from 6.9 g of benzophenonehydrazone, 7.6 g of mercuric oxide (yellow) and 70 ml of n-hexane, in 30 ml of methylene chloride solution, and the mixture was stirred at room temperature overnight. After the reaction mixture was condensed, ether was added thereto to crystalize, and crystal was collected by filtration and dried to obtain 7.28 g of the title compound.

$^1$H NMR (d$_6$-DMSO+CDCl$_3$) δ: 3.75 (broad s, 2H), 4.34 (broad s, 2H), 4.77 to 5.34 (m, 6H), 6.96 to 7.75 (m, 12H).

Example 43

Synthesis of sodium 7-{2-[2-amino-1,3-thiazol-4-yl]-2-[1-(3-(3,4-dihydroxybenzoyl)carbazoyl)-1-methylethoxyimino]acetamido}-3-[(2,5-bis(hydroxymethyl)-s-triazolo[1,5-a]pyrimidin-7-yl)thiomethyl]-3-cephem-4-carboxylate In 30 ml of DMF were dissolved 3.22 g of 2-(2-amino-1,3-thiazol-4-yl)-2-{1-[3-(3,4-dihydroxybenzoyl)carbazoyl]-1-methylethoxyimino}acetic acid.hydrochloride, 5.32 g of diphenylmethyl 7-amino-3-[(2,5-bis(hydroxymethyl)-s-triazolo[1,5-a]pyrimidin-7-yl)thiomethyl]-3-cephem-4-carboxylate obtained in Example 42 and 1.38 g of 1-hydroxybenzotriazole and ice-cooled. Then, 1.86 g of DCC was added thereto and the mixture was stirred for 15 minutes under ice-cooling, and further stirred at room temperature for one hour. After the reaction mixture was filtered, 15 ml of chloroform was added thereto and the mixture was added dropwise into 2 liters of ether, precipitates were collected by filtration, washed with ether and then dried. Powder obtained was purified through silica gel column chromatography to obtain powder. A mixed solution of 30 ml of trifluoroacetic acid and 8 ml of anisole was ice-cooled and the powder previously obtained was added thereto, and the mixture was stirred for 30 minutes and added dropwise into 400 ml of ether. Precipitates were collected by filtration, washed with ether and then dried to obtain powder. The powder was suspended in 200 ml of water and dissolved at pH 7 by adding a 5% sodium hydrogencarbonate solution. After the resulting solution was adsorbed to 200 ml of HP 20 column filled with water, it was washed with water. Subsequently, the mixture was eluted with a 50% methanol-water. After evaporation of methanol, the residue was freeze-dried to obtain 4.16 g of the title compound.

$^1$H NMR (d$_6$-DMSO) δ: 1.60 (s, 6H), 3.86 (broad s, 2H), 4.60 (broad s, 2H), 4.78 (s, 4H), 5.40 (d, J=5 Hz, 1H), 5.87 to 6.27 (m, 1H), 6.94 to 7.72 (m, 5H).

Example 44

Synthesis of 7-[2-(2-amino-1,3-thiazol-4-yl)-2-(1-carbazoyl-1-methylethoxyimino)acetamido]-3-[(2-hydroxymethyl-5-methyl-s-triazolo[1,5-a]pyrimidin-7-yl)thiomethyl]-3-cephem-4-carboxylate.dihydrochloride In 35 ml of DMF were dissolved 2.5 g of 2-(2-formylamino-1,3-thiazol-4-yl)-2-[1-(3-formylcarbazoyl)-1-methylethoxyimino]acetic acid, 5 g of diphenylmethyl 7-amino-3-[(2-hydroxymethyl-5-methyl-s-triazolo[1,5-a]pyrimidin-7-yl)thiomethyl]-3-cephem-4-carboxylate and 1.33 g of 1-hydroxybenzotriazole and the solution was ice-cooled. To the solution was added 1.8 g of DCC, and the mixture was stirred under ice-cooling for 10 minutes and further stirred at room temperature for one hour. After filtration of the reaction mixture, 10 ml of chloroform was added to the filtrate and the mixture was added dropwise into one liter of ether. Precipitates were collected by filtration, washed with ether and dried to obtain a powder. This powder was purified through a column filled with 50 g of silica gel to obtain a powder. A mixed solution of 30 ml of trifluoroacetic acid, 8 ml of anisole and 15 ml of methylene chloride was ice-cooled, and the powder previously obtained was added to the mixed solution and the mixture was stirred for 30 minutes. This reaction mixture was added dropwise into 400 ml of ether, precipitates were collected by filtration and dried to obtain 4.15 g of the title compound.

$^1$H NMR (d$_6$-DMSO) δ: 1.61 (s, 6H), 2.68 (s, 3H), 3.83 (s, 2H), 4.60 (broad s, 2H), 4.78 (s, 2H), 5.37 (d, J=5 Hz, 1H), 5.80 to 6.18 (m, 1H), 7.27 (s, 1H), 7.60 (s, 1H).

Example 45

Synthesis of sodium 7-{2-[2-amino-1,3-thiazol-4-yl]-2-[1-(3-(3,4-dihydroxybenzylidene)carbazoyl)-1-methylethoxyimino]acetamido}-3-[(2-hydroxymethyl-5-methyl-s-triazolo[1,5-a]pyrimidin-7-yl)thiomethyl]-3-cephem-4-carboxylate In 40 ml of methanol was dissolved 3.8 g of 7-[2-(2-a mino-1,3-thiazol-4-yl)-2-(1-carbazoyl-1-methylethoxyimino)acetamido]-3-[(2-hydroxymethyl-5-methyl-s-triazolo[1,5-a]pyrimidin-7-yl)thiomethyl]-3-cephem-4-carboxylate.dihydrochloride, and then 1.03 g of protocatechuic aldehyde was added to the solution and the mixture was stirred at room temperature for 1.5 hours. The mixture was poured into 400 ml of ether and precipitates were collected by filtration, washed with ether and dried to obtain a powder. The powder was suspended in 100 ml of water and dissolved at pH 6 by addition of a 5% sodium hydrogencarbonate solution. After the resulting solution was adsorbed to 100 ml of HP 20 column filled with water, it was washed with water. Subsequently, the mixture was eluted with methanol-water. After conensation of fractions containing the title compound, the residue was freeze-dried to obtain 3.15 g of the title compound.

$^1$H NMR (d$_6$-DMSO) δ: 1.63 (s, 6H), 2.68 (s, 3H), 3.82 (broad s, 2H), 4.62 (broad s, 2H), 4.62 (broad s, 2H), 4.82 (s, 2H), 5.40 (d, J=5 Hz, 1H), 5.92 to 6.22 (m, 1H), 6.98 to 7.76 (m, 5H), 8.58 (s, 1H).

Example 46

Synthesis of pivaloyloxymethyl 7-amino-3-[(2-methoxymethyl-5-methyl-s-triazolo[1,5-a]pyrimidin-7-yl)thiomethyl]-3-cephem-4-carboxylate In 80 ml of acetone was suspended 16.9 g of 7-amino-3-[(2-methoxymethyl-5-methyl-s-triazolo[1,5-a]pyrimidin-7yl)thiomethyl]-3-cephem-4-carboxylic acid and ice-cooled, and then 5.98 ml of 1,5-diazabicyclo[5.4.-0]undec-5-ene (DBU) was added dropwise to the solution and the mixture was stirred for 30 minutes. After 9.68 g of pivaloyloxymethyl iodide was added dropwise to the mixture, the mixture was stirred at room temperature for 20 minutes. After the reaction mixture was poured into a mixed solution of 280 ml of ethyl acetate and 200 ml of water and stirred, an organic layer was separated therefrom, washed with water, further washed with a saturated saline solution and dried over anhydrous magnesium sulfate. By removing a solvent, an oily product was obtained. This oily product was purified through silica gel column chromatography. To the oily product obtained was added ether to powderize, and it was collected by filtration and dried to obtain 10.17 g of the title compound.

$^1$H NMR (d$_6$-CDCl$_3$) δ: 1.22 (s, 9H), 2.68 (s, 3H), 3.57 (s, 3H), 3.72 (s, 2H), 4.43 (s, 2H), 4.77 (s, 2H), 4.96 (ABq, 2H), 5.96 (broad s, 2H), 7.02 (s, 1H).

Example 47

Synthesis of pivaloyloxymethyl 7-[2-(2-amino-1,3-thiazol-4-yl)-2-methoxyiminoacetamido]-3-[(2-methoxymethyl-5-methyl-s-triazolo[1,5-a]pyrimidin-7-yl)thiomethyl]-3-cephem-4-carboxylate In 50 ml of DMF were added 3.43 g of 2-(2-formylamino1,3-thiazol-4-yl)-2-methoxyiminoacetic acid, 10.1 g of pivaloyloxymethyl 7-amino-3-[(2-methoxymethyl-5-methyl-s-triazolo[1,5-a]pyrimidin-7-yl)thiomethyl]-3-cephem-4-carboxylate and 2.76 g of 1-hydroxybenzotriazole and ice-cooled, and 3.71 g of DCC was added to the solution and the mixture was stirred for 1.5 hours under ice-cooling. After filtration of the reaction mixture, 20 ml of chloroform was added to the filtrate, and the mixture was added dropwise into 4 liters of ether. Precipitates were collected by filtration and dried to obtain a powder. To 1.57 ml of phosphorus oxychloride was added 80 ml of ice-cooled methanol, and the powder previously obtained was added thereto and the mixture was stirred for 1.5 hours under ice-cooling. After the mixture was condensed to a half, the residue was added dropwise to a mixed solution of 200 ml of water and 200 ml of ethyl acetate and the mixture was neutralized with addition of sodium hydrogencarbonate. An organic layer was separated, washed with water and then dried over anhydrous magnesium sulfate, followed by evaporation of a solvent to obtain an oily product. The oily product was purified through silica gel column chromatography. To the oily product obtained was added ether to powderize, and it was collected by filtration and dried to obtain 3.4 g of the title compound.

$^1$H NMR (d$_6$-DMSO) δ: 1.20 (s, 9H), 2.62 (s, 3H), 3.42 (s, 3H), 3.79 (bs, 2H), 4.02 (s, 3H), 4.48 (bs, 2H), 4.65 (s,

2H), 5.28 (d, J=5 Hz, 1H), 5.73 to 6.16 (m, 3H), 6.96 (s, 1H), 7.42 (s, 1H).

Example 48

Synthesis of 7-[2-(2-amino-1,3-thiazol-4-yl)-2-(1-carbazoyl-1-methylethoxyimino)acetamido]-3-[(2-methoxymethyl-5-methyl-s-triazolo[1,5-a]pyrimidin-7-yl)thiomethyl]-3-cephem-4-carboxylate.dihydrochloride In 35 ml of DMF were dissolved 2.5 g of 2-(2-formylamino1,3-thiazol-4-yl)-2-[1-(3-formylcarbazoyl)-1-methylethyloxyimino]acetic acid, 5.12 g of diphenylmethyl 7-amino-3-[(2-methoxymethyl-5-methyl-s-triazolo[1,5-a]pyrimidin-7-yl)thiomethyl]-3-cephem-4-carboxylate and 1.33 g of 1-hydroxybenzotriazole and the solution was ice-cooled. To the solution was added 1.8 g of DCC, and the mixture was stirred under ice-cooling for 10 minutes and further stirred at room temperature for one hour. After filtration of the reaction mixture, 10 ml of chloroform was added to the filtrate and the mixture was added dropwise into one liter of ether, precipitates were collected by filtration, washed with ether and dried to obtain a powder. This powder was purified through a column filled with 50 g of silica gel to obtain a powder. A mixed solution of 30 ml of trifluoroacetic acid, 8 ml of anisole and 15 ml of methylene chloride was ice-cooled, and the powder previously obtained was added to the mixed solution and the mixture was stirred for 30 minutes. This reaction mixture was added dropwise into 400 ml of ether, precipitates were collected by filtration and dried to obtain a powder. To 1.45 ml of phosphorus oxychloride was added 40 ml of ice-cooled methanol, and the powder previously obtained was added thereto and the mixture was stirred for one hour under ice-cooling. The mixture was added dropwise into 400 ml of ether, precipitates were collected by filtration and dried to obtain 4.0 g of the title compound.

$^1$H NMR (d$_6$-DMSO) δ: 1.63 (s, 6H), 2.69 (s, 3H), 3.48 (s, 3H), 3.88 (s, 2H), 4.61 (broad s, 2H), 4.76 (s, 2H), 5.42 (d, J=5 Hz, 1H), 5.87 to 6.21 (m, 1H), 7.30 (s, 1H), 7.58 (s, 1H).

Test example 1

20 mg/kg of compound obtained in the above Example 19 was administered parenterally to cynomolgus monkeys and the half-life in blood was measured. The results are shown in Table 1.

The concentration of the compound was measured according to HPLC method. Novapack C18 or Microbondapack C18 (both trade name, produced by Waters Co.) was used for analysis. Further, cefpiramide was used as a control drug.

TABLE 1

| Compound | Half-life in blood of cynomolgus monkeys (hours) |
|---|---|
| Example 19 | 2.6 |
| Cefpiramide | 2.5 |

As is apparent from Table 1, the half-life in blood of the compound according to the present invention is the same as that of cefpiramide in the case of cynomolgus monkeys. Among the existing cephalosporins, cefpiramide is known as a cephalosporin having a long half-life in blood. On the other hand, the experimental results that the half-life in blood of β-lactam compounds in monkey and human being are mutually well-related has been reported by U. Sawada et al. (J. Pharmaco., Biopharma., 12, 241 (1984)). Accordingly, the results in Table 1 suggest that the half-life in blood of said compound would be the same as that of cefpiramide for human beings. High usefulness such that the same or higher clinical efficacy could be obtained with a smaller number of administration, when compared with other many cephalosporins having shorter half-life, can be expected.

Test example 2

The minimum inhibitory concentration (MIC) of the compounds obtained in the above Examples were measured according to the standard method of Japan Society of Chemotherapy. The results are shown in Tables 2A and 2B and Table 3.

In Tables 2A and 2B and Table 3, ceftazidime (CAZ) was used as a control compound.

As is apparent from Tables 2A and 2B, the compound of the present invention is effective to gram positive bacteria and gram negative bacteria and has wide range of antibacterial spectrum. Particularly, the compound of the present invention exhibits stronger antibacterial activities against glucose non-fermenting bacteria including Pseudomonas aeruginosa than the third generation cephalosporin.

As is apparent from Table 3, the compound of the present invention exhibits strong antibacterial activities against clinical isolates resistant to ceftazidime, one of the third generation cephalosporins.

TABLE 2A

| Strain | MIC (μg/ml) | | | | | | |
|---|---|---|---|---|---|---|---|
| | Example 19 | Example 25 | Example 31 | Example 38 | Example 43 | Example 45 | CAZ |
| Staphylococcus aureus Smith | 1.56 | 3.13 | 12.5 | 3.13 | 3.13 | 3.13 | 6.25 |
| Staphylococcus aureus IAA498 | 6.25 | 6.25 | 25 | 6.25 | 6.25 | 6.25 | 12.5 |
| Escherichia coli ML4704 | 0.012 | 0.025 | 0.025 | 0.1 | 0.1 | 0.39 | 0.05 |
| Escherichia coli GN5482 | 0.025 | 0.025 | 0.05 | 0.05 | 0.1 | 0.1 | 1.56 |
| Klebsiella pneumoniae 4at521 | 0.012 | 0.025 | 0.025 | 0.012 | 0.2 | 0.39 | 0.1 |
| Enterobacter cloacae GN7471 | 6.25 | 3.13 | 0.78 | 1.56 | 1.56 | 1.56 | 3.13 |
| Enterobacter cloacae 908RN | 6.25 | 6.25 | 1.56 | 1.56 | 3.13 | 12.5 | 100 |
| Citrobacter freundii GN7391 | 12.5 | 12.5 | 1.56 | 6.25 | 6.25 | 12.5 | >100 |
| Serratia marcescens GN10857 | 0.78 | 0.39 | 0.78 | 0.39 | 0.39 | 0.78 | 3.13 |
| Proteus vulgris GN7919 | 1.56 | 1.56 | 3.13 | 1.56 | 3.13 | 12.5 | 1.56 |
| Pseudomonas aeruginosa GN10362 | 0.05 | 0.05 | 0.025 | 0.1 | 0.1 | 0.78 | 1.56 |
| Pseudomonas aeruginosa 4au542 | 0.2 | 0.2 | 0.2 | 0.2 | 0.2 | 0.78 | 3.13 |
| Pseudomonas aeruginosa 5D58-1 | 0.05 | 0.05 | 0.1 | 0.1 | 0.1 | 0.39 | 1.56 |
| Pseudomonas cepacia OF189 | 0.025 | — | — | 0.025 | 0.025 | 0.2 | 6.25 |
| Pseudomonas maltophilia OF247 | 0.39 | — | — | 0.39 | 0.78 | 12.5 | 3.13 |

TABLE 2B

| Strain | Example 21 | Example 18 | Example 27 | Example 32 | Example 44 | Example 48 | Example 39 | CAZ |
|---|---|---|---|---|---|---|---|---|
| *Staphylococcus aureus* Smith | 3.13 | 0.39 | 0.78 | 6.25 | 6.25 | 6.25 | 0.78 | 6.25 |
| *Staphylococcus aureus* IAA498 | 6.25 | 12.5 | 25 | 12.5 | 12.5 | 12.5 | 12.5 | 12.5 |
| *Escherichia coli* ML4704 | 0.39 | 0.025 | 0.05 | 0.1 | 0.2 | 0.2 | 0.05 | 0.05 |
| *Escherichia coli* GN5482 | 0.78 | 0.1 | 0.39 | 0.2 | 0.39 | 0.78 | 0.1 | 1.56 |
| *Klebsiella pneumoniae* 4at521 | 0.78 | 0.39 | 1.56 | 0.2 | 3.13 | 6.25 | 0.78 | 0.1 |
| *Enterobacter cloacae* GN7471 | 6.25 | 3.13 | 6.25 | 6.25 | 25 | 50 | 3.13 | 3.13 |
| *Enterobacter cloacae* 908RN | 100 | 50 | 50 | 100 | >100 | >100 | 50 | 100 |
| *Citrobacter freundii* GN7391 | >100 | 50 | 50 | 100 | 100 | >100 | 25 | >100 |
| *Serratia marcescens* GN10857 | 12.5 | 12.5 | 25 | 25 | 50 | 100 | 25 | 3.13 |
| *Proteus vulgris* GN7919 | 3.13 | 25 | 25 | 50 | 50 | 50 | 6.25 | 1.56 |
| *Pseudomonas aeruginosa* GN10362 | 12.5 | 100 | 100 | 100 | 25 | 50 | 100 | 1.56 |
| *Pseudomonas aeruginosa* 4au542 | 12.5 | 100 | >100 | >100 | 100 | >100 | >100 | 3.13 |
| *Pseudomonas aeruginosa* 5D58-1 | 6.25 | 100 | 100 | >100 | 25 | 50 | 100 | 1.56 |
| *Pseudomonas cepacia* OF189 | — | — | — | — | 50 | 100 | 25 | 6.25 |
| *Pseudomonas maltophilia* OF247 | — | — | — | — | 50 | 100 | 50 | 3.13 |

TABLE 3

| | MIC (μg/ml) | |
|---|---|---|
| Strain | Example 19 | CAZ |
| *Enterobacter cloacae* 5D52-2 | 0.39 | 12.5 |
| *Enterobacter cloacae* 5D83-2 | 0.78 | 12.5 |
| *Enterobacter cloacae* IV25 | 1.56 | 50 |
| *Enterobacter cloacae* IY247 | 6.25 | 12.5 |
| *Enterobacter cloacae* 908RN | 12.5 | >100 |
| *Citrobacter freundii* 5D60-1 | 1.56 | >100 |
| *Citrobacter freundii* 1R523 | 0.78 | 25 |
| *Citrobacter freundii* 1R524 | 0.39 | 25 |
| *Citrobacter freundii* 1R526 | 0.39 | 25 |
| *Citrobacter freundii* 1R527 | 0.2 | 25 |
| *Citrobacter freundii* 1U589 | 1.56 | 100 |
| *Citrobacter freundii* 1U592 | 25 | 100 |
| *Citrobacter freundii* GM7391 | 6.25 | >100 |

Example 49

The following pharmaceutical for injection was prepared.

Sodium 7-{2-[2-amino-1,3-thiazol-4-yl]-2-[1-(3-(3,4-dihydroxybenzoyl)carbamoyl)-1-methylethoxyimino]acetamido}-3-[(2-hydroxymethyl-5-methyl-s-triazolo[1,5-a]pyrimidin-7-yl)thiomethyl]-3-cephem-4-carboxylate obtained in Example 19 ... 500 mg Sterile distilled water ... amount so as to give a total of about 5 ml.

The above compound was dissolved in the sterile distilled water to obtain the pharmaceutical for injection.

We claim:

1. A compound represented by the formula (VII'):

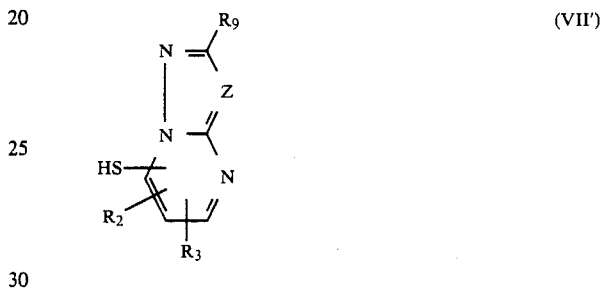

where at least one of $R_2$, $R_3$ and $R_9$ represent a group represented by the formula: —A—$OR_4$ where $R_4$ represents a hydrogen or a lower alkyl group; and A represents a straight or branched alkylene group having 1 to 6 carbon atoms; and a remaining group or groups are each independently a hydrogen atom; a cyano group; a lower alkyl group which may be substituted by a halogen atom; a carbamoyl group which may be substituted by a lower alkyl group; a cycloalkyl group; or a carboxyl group which may be substituted by a protective group or an eliminatable group which is easily hydrolyzable in a human body, and also when $R_9$ is —A—$OR_4$, $R_2$ and $R_3$ may be combined with each other to form an alkylene group having 3 to 4 carbon atoms; Z represents a nitrogen atom or a group represented by the formula: C—$R_{10}$ where $R_{10}$ represents a hydrogen atom, a carboxyl group or a lower alkyl group which may be substituted by a hydroxy group or a lower alkoxy group; and X represents a hydrogen atom, a lower alkyl group, a lower alkoxy group or a halogen atom.

2. A compound according to claim 1, wherein the protective group is selected from the group consisting of a diphenylmethyl group, a t-butyl group, a p-nitrobenzyl group and a trimethylsilyl group and the eliminatable group which is easily hydrolyzable in a human body is selected from the group consisting of an acetoxymethyl group, an α-acetoxyethyl group, a pivaroyloxymethyl group, an ethoxycarbonyloxymethyl group, an α-methoxycarbonyloxymethyl group, an α-methoxycarbonyloxyethyl group, an α-ethoxycarbonyloxyethyl group, a 1-indanyl, a phthalidyl group, and a 5-methyl-2-oxo-1,3-dioxol-4-yl-methyl group.

3. A compound according to claim 2, wherein the cycloalkyl group is selected from the group consisting of a cyclopropyl group, a cyclobutyl group, a cyclopentyl group and a cyclohexyl group.

* * * * *